United States Patent
Manneck et al.

(10) Patent No.: US 10,265,252 B2
(45) Date of Patent: Apr. 23, 2019

(54) ODOR-REDUCING DEVELOPER FOR OXIDATION DYES

(71) Applicant: Henkel AG & Co. KGaA, Duesseldorf (DE)

(72) Inventors: Hartmut Manneck, Barnitz (DE); Stefan Hoepfner, Hamburg (DE); Matthias Schweinsberg, Langenfeld (DE); Astrid Kleen-Fehres, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 19 days.

(21) Appl. No.: 15/539,063

(22) PCT Filed: Nov. 2, 2015

(86) PCT No.: PCT/EP2015/075430
§ 371 (c)(1),
(2) Date: Jun. 22, 2017

(87) PCT Pub. No.: WO2016/102107
PCT Pub. Date: Jun. 30, 2016

(65) Prior Publication Data
US 2017/0340531 A1    Nov. 30, 2017

(30) Foreign Application Priority Data

Dec. 22, 2014  (DE) .................. 10 2014 226 747

(51) Int. Cl.
| | | |
|---|---|---|
| A61Q 5/10 | (2006.01) | |
| A61K 8/22 | (2006.01) | |
| A61K 8/34 | (2006.01) | |
| A61K 8/37 | (2006.01) | |
| A61K 8/39 | (2006.01) | |
| A61Q 5/08 | (2006.01) | |
| A61K 8/86 | (2006.01) | |

(52) U.S. Cl.
CPC ................ *A61K 8/22* (2013.01); *A61K 8/342* (2013.01); *A61K 8/345* (2013.01); *A61K 8/375* (2013.01); *A61K 8/39* (2013.01); *A61K 8/86* (2013.01); *A61Q 5/08* (2013.01); *A61Q 5/10* (2013.01)

(58) Field of Classification Search
CPC ... A61Q 5/10; A61Q 5/08; A61K 8/22; A61K 8/342; A61K 8/345; A61K 8/86; A61K 8/39; A61K 8/375

See application file for complete search history.

(56) References Cited

U.S. PATENT DOCUMENTS

2015/0272845 A1* 10/2015 Neuba .................... A61K 8/342
                                                                  424/62
2016/0151266 A1    6/2016 Neuba et al.

FOREIGN PATENT DOCUMENTS

| DE | 19756454 C1 | 6/1999 | |
|---|---|---|---|
| WO | WO 2014/090645 A2 * | 6/2014 | ............... A61K 8/34 |

OTHER PUBLICATIONS

STIC Search Report dated Oct. 12, 2016.*
EPO, International Search Report and Written Opinion issued in International Application No. PCT/EP2015/075430, dated Dec. 17, 2015.

* cited by examiner

*Primary Examiner* — Eisa B Elhilo
(74) *Attorney, Agent, or Firm* — Lorenz & Kopf, LLP

(57) ABSTRACT

The aim of the present disclosure was to provide an improved oxidizing agent preparation for oxidative color modifying agents, which are present as soap based gels and contain ammonia as the alkalizing agent and optionally at least one oxidation dye precursor, and have a pH in the range of from 8 to 11.5, measured at 20° C., with which homogeneous and viscosity-stable application mixtures can be produced that release less ammonia during the entire leave-in time. It was surprisingly found that aqueous hydrogen peroxide preparations which contain selected 1-alkanols, glyceryl fatty acid esters, ethoxylated fatty alcohols, polyols and oils, achieve said aim in a very satisfactory manner.

20 Claims, No Drawings

ODOR-REDUCING DEVELOPER FOR OXIDATION DYES

CROSS-REFERENCE TO RELATED APPLICATION

This application is a U.S. National-Stage entry under 35 U.S.C. § 371 based on International Application No. PCT/EP2015/075430, filed Nov. 2, 2015 which was published under PCT Article 21(2) and which claims priority to German Application No. 102014226747.1, filed Dec. 22, 2014, which are all hereby incorporated in their entirety by reference.

TECHNICAL FIELD

The present application relates to compositions, which are suitable as oxidizing agent for soap-gel-based hair brightening and/or hair dyeing preparation, wherein the soap-gel based hair brightening and/or hair dyeing preparations contain ammonia or ammonium hydroxide as alkalizing agent and optionally at least one oxidation dye precursor and have a pH ranging from about 8 to about 11.5, measured at 20° C.

BACKGROUND

The application properties of the application mixture, especially the release and odor of ammonia can be reduced clearly with the oxidizing agents as contemplated herein.

A further object of the present application relates to a composition for changing the color of keratinic fibers, which aforementioned composition can be produced from two compositions, which are separated from one another, by mixing these two compositions, wherein one of the two compositions is an oxidative composition of the first subject matter of the application and the second composition is a soap-gel-based hair brightening and/or hair dyeing preparation, which contains ammonium hydroxide as alkalizing agent and optionally an oxidation dye precursor and has a pH ranging from about 8 to about 11.5, measured at 20° C., and, furthermore preferably, contains from about 25-about 85% by weight of water, furthermore from about 5-about 20% by weight and preferably from about 8-about 16% by weight of at least one salt of a $C_{12}$-$C_{22}$ fatty acid, preferably a salt of oleic acid, optionally from about 0.1-about 3% by weight of an anionic surfactant, selected from alkyl sulfates, alkyl ether sulfates and ether carboxylic acids with 10 to 20 carbon atoms in the alkyl group and up to 16 glycol ether groups in the molecule, from about 2-about 20% by weight and preferably from about 3-about 16% by weight of at least one polyethylene glycol ether of a linear, saturated or unsaturated $C_{10}$-$C_{18}$ alkanols with 1-5 ethylene oxide units in the molecule, a total of from about 0-about 1% by weight of at least one oil, preferably at least one organic solvent selected from monohydric to tetrahydric $C_2$-$C_6$ alcohols, in a total amount of from about 0.1-about 35% by weight and optionally at least one oxidation dye precursor, wherein all quantitative data is related to the weight of the composition (A).

A further subject matter of the present application relates to a kit for the oxidative color change of keratin fibers, comprising a soap gel-based, optionally a dye-containing, ammonia-containing, alkalizing preparation and an aqueous hydrogen peroxide preparation, wherein the hydrogen peroxide preparation is optimized in that the ready-to-use mixture of alkalizing gel and hydrogen peroxide preparation represents a viscous cream or paste with the viscosity ranging from about 2000 to about 5000 mPas (for example, measured at 20° C. with a Haake-viscosimeter Type MV2 at a speed of 8 RPM), which can be applied well on the fibers, which are to be brightened and/or dyed and, during the application time of from about 5 to about 60 minutes, have a reduced release of ammonia.

A further subject matter of the present application relates to a process for the oxidative color change of keratin fibers, wherein the ready-to-use bleaching and/or coloring agent is prepared by mixing the components of the abovementioned kit immediately before the application, subsequently applying it to the fibers, in particular, to the hair and, after an exposure time of from about 5 to about 60 minutes, rinsing it off once again.

The present disclosure relates to the oxidative color change of keratinic fibers, especially of hair. Since melanin dye of the fibers is destroyed to a certain extent during the treatment of keratinic fibers, especially hair, with oxidizing agents, in particular with hydrogen peroxide, the fibers/hair inevitably is brightened, that is, the color thereof is changed even in the absence of a dye. Therefore, for the purpose of the present application, the term "color change" encompasses both the brightening and the coloring with one or more dyes.

Someone of ordinary skill in the art knows various methods for changing the color of human hair. In general, for dyeing human hair, either substantive dyes or oxidation dyes are used, which are formed by the oxidative coupling of one or more developer components with one another or with one or more coupler components. Coupler and developer components are also referred to as oxidation dye precursors. The dyeings, achieved with oxidation dyes, usually are referred to as permanent or semi-permanent dyeings.

These compositions generally contain hydrogen peroxide as oxidizing agent. Since hydrogen peroxide is not sufficiently stable in the alkaline pH range, oxidative dyes usually are composed of two components, which are mixed with one another immediately before use. The one component contains hydrogen peroxide in an aqueous solution or emulsion, this composition having an acidic pH value ranging from about 2.5 to about 5.5 to stabilize the hydrogen peroxide. The second component contains one or more alkalizing agents in such an amount, that the application mixture of the two components has a pH ranging from about 8 to about 11. If the alkalization preparation contains no dye or only a small amount of dye, the latter is used for laminating unwanted color shades, which may arise during the oxidation of melanin, since this is a whitening agent or bleaching agent. However, the alkalizing preparation may also contain oxidation dye precursors and/or substantive dyes; the resulting application mixture then serves as a dye. There are also coloring kits and dyeing processes, in which the application mixture of the two components has a pH ranging from about 6 to about 7.9; however, the color results of these so-called "acidic" dyeings frequently do not reach the good results obtained with alkaline application mixtures.

Especially in the North American market, ammonia-containing alkalizing preparations, which are present as a soap-based gel and especially larger amounts of soaps, that is, salts of fatty acids, and possibly other surfactants, preferably are used for oxidatively changing hair color; however, for example, they contain hardly any or only a few fatty alcohols. Compounds of this kind have a very strong smell of ammonia when compared to fatty alcohol-containing blonding or dyeing creams when applied to the hair.

Furthermore, the alkalizing preparations contain ammonia as alkalizing agent and optionally at least one oxidation dye precursor and has a pH ranging from about 8 to about 11.5, measured at 20° C.

Furthermore, preferably alkalizing preparations are used, which contain from about 25-about 85% by weight of water, furthermore from about 5-about 20% by weight and preferably from about 8-about 16% by weight of at least one salt of a $C_{12}$-$C_{22}$ fatty acid, preferably a salt of oleic acid, optionally from about 0.1-about 3% by weight of an anionic surfactant selected from alkyl sulfates, alkyl ether sulfates and ether carboxylic acids with from about 10 to about 20 carbon atoms in the alkyl group and up to 16 glycol ether groups in the molecule, from about 2-about 20% and preferably from about 3-about 16% by weight of at least one polyethylene glycol ether of linear, saturated or unsaturated $C_{10}$-$C_{18}$ alkanols with 1-5 ethylene oxide units in the molecule, a total of from about 0-about 1% by weight of at least one oil, preferably at least one organic solvent, selected from monohydric to tetrahydric $C_2$-$C_6$ alcohols, especially preferably in a total amount of from about 0.1-about 35% by weight and optionally at least one oxidation dye precursor, wherein all quantitative data is related to the weight of the composition (A).

Usually, for the oxidative change in hair color, the alkalizing preparation is mixed with an aqueous oxidizing agent preparation, for example, in a re-closable bottle or a shaker beaker, and the therefrom resulting application mixture is applied on the hair to be treated, where it remains for an exposure time of from about 5 to about 60 minutes before it is rinsed off once again.

In the prior art, various solvent formulations are already known in order to reduce the odor of ammonia of a hair treatment composition. For example, instead of ammonia, an alkanolamines, such as monoethanolamine, which is highly volatile, may be used and smells less strongly than ammonia. However, it has turned out that the ability of keratin fibers to absorb dyes is best when ammonia is used. If the same color result is to be achieved with monoethanolamine, more hydrogen peroxide must be used or the application mixture must be left to act for a longer time on the keratin fibers. In the end, the use of monoethanolamine leads to greater damage to the keratin fibers than does the use of ammonia.

A different possibility for reducing the odor of the application mixture is to mask the smell of ammonia by using larger amounts of perfume. However, because of the piercing odor of ammonia, this is difficult to achieve.

BRIEF SUMMARY

Oxidizing compositions for the oxidative treatment of hair, kits for oxidatively changing the color of keratinic fibers, and methods for oxidatively changing the color of keratinic fibers are provided herein. In an embodiment, an oxidizing composition for the oxidative treatment of hair includes from about 50-about 96% by weight of water, from about 0.5-about 20% by weight of hydrogen peroxide, at least one linear, saturated 1-alkanol with 12-30 carbon atoms, at least one glyceryl fatty ester of the general Formula (I),

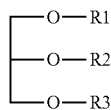

wherein R1, R2 and R3, independently of one another represent a hydrogen atom or a group of Formula (II),

wherein R4 represents a linear or branched, saturated or unsaturated $C_{11}$-$C_{27}$ alkyl group, with the proviso that at least one and not more than two groups are selected from R1, R2 and R3 of a grouping of Formula (II), at least one ethoxylated fatty alcohol of Formula (III)

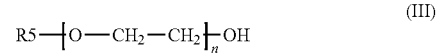

wherein R5 represents a linear or branched, saturated or unsaturated $C_8$-$C_{24}$ alkyl group and n represents a whole number from 10 to 30, at least one ethoxylated fatty alcohol of Formula (IV)

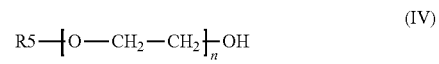

wherein R5 represents a linear or branched, saturated or unsaturated $C_8$-$C_{24}$ alkyl group and n represents a whole number from 50 to 150, at least one polyol selected from $C_2$-$C_9$ alkanols with 2-6 hydroxyl groups, polyethylene glycols with 3-20 ethylene oxide units, or mixtures thereof, and at least one oil, wherein all quantitative data is related to the weight of the oxidizing composition.

In another embodiment, a kit for oxidatively changing the color of keratinic fibers includes two compositions (A) and (B) contained separately from one another. The composition (B) is an oxidizing composition including from about 50-about 96% by weight of water, from about 0.5-about 20% by weight of hydrogen peroxide, at least one linear, saturated 1-alkanol with 12-30 carbon atoms, at least one glyceryl fatty ester of the general Formula (I),

wherein R1, R2 and R3, independently of one another represent a hydrogen atom or a group of Formula (II),

wherein R4 represents a linear or branched, saturated or unsaturated $C_{11}$-$C_{27}$ alkyl group, with the proviso that at least one and not more than two groups are selected from R1, R2 and R3 of a grouping of Formula (II), at least one ethoxylated fatty alcohol of Formula (III)

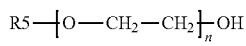

wherein R5 represents a linear or branched, saturated or unsaturated $C_8$-$C_{24}$ alkyl group and n represents a whole number from 10 to 30, at least one ethoxylated fatty alcohol of Formula (IV)

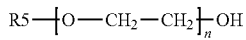

wherein R5 represents a linear or branched, saturated or unsaturated $C_8$-$C_{24}$ alkyl group and n represents a whole number from 50 to 150, at least one polyol, selected from $C_2$-$C_9$ alkanols with 2-6 hydroxyl groups, polyethylene glycols with 3-20 ethylene oxide units, or mixtures thereof, and at least one oil, wherein all quantitative data is related to the weight of the oxidizing composition. The composition (A) is present in the form of a soap-based gel and includes from about 25-about 85% by weight of water, ammonia, from about 5-about 20% by weight of a salt of a $C_{12}$-$C_{22}$ fatty acid, from about 2-about 20% by weight of at least one polyethylene glycol ether of a linear, saturated or unsaturated $C_{10}$-$_{18}$ alkanols with 1-5 ethylene oxide units in the molecule, a total of from about 0-about 1% by weight of at least one oil, optionally at least one organic solvent, selected from a monohydric to tetrahydric $C_2$-$C_6$ alcohols, optionally from about 0.1-about 3% by weight of an anionic surfactant selected from alkyl sulfates, alkyl ether sulfates and ether carboxylic acids with 10 to 20 carbon atoms in the alkyl group and up to 16 glycol ether groups in the molecule, optionally at least one oxidizing dye precursor, wherein all quantitative data is based on the weight of the composition (A). Composition (A) has a pH ranging of from about 8 to about 11.5, measured at 20° C.

In another embodiment, a method of oxidatively changing the color of keratinic fibers includes providing an oxidizing composition (B) that includes from about 50-about 96% by weight of water, from about 0.5-about 20% by weight of hydrogen peroxide, at least one linear, saturated 1-alkanol with 12-30 carbon atoms, at least one glyceryl fatty acid ester of the general Formula (I),

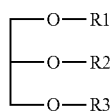

wherein R1, R2 and R3 independently of one another represent a hydrogen atom or a group of Formula (II)

wherein R4 represents a linear or branched, saturated or unsaturated $C_{11}$-$C_{27}$ alkyl group, with the proviso that at least one and not more than two groups are selected from R1, R2 and R3 of a grouping of Formula (II), at least one ethoxylated fatty alcohol of Formula (III)

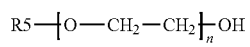

wherein R5 represents a linear or branched, saturated or unsaturated $C_8$-$C_{24}$ alkyl group and n represents a whole number from 10 to 30, at least one ethoxylated fatty alcohol of Formula (IV)

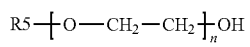

wherein R5 represents an linear or branched, saturated or unsaturated $C_8$-$C_{24}$ alkyl group and n represents a whole number from about 50 to about 150, at least one polyol selected from $C_2$-$C_9$ alkanols with 2-6 hydroxyl groups, polyethylene glycols with 3-20 ethylene oxide units, or mixtures thereof, and at least one oil, wherein all quantitative data is related to the weight of the oxidizing composition. A composition (A) is provided, which is present in the form of a soap-based gel and includes from about 25-about 85% by weight of water, ammonia, from about 5-about 20% by weight of at least one salt of a $C_{12}$-$C_{22}$ fatty acid, from about 2-about 20% of at least one polyethylene glycol ether of a linear, saturated or unsaturated $C_{10}$-$C_{18}$ alkanols with 1-5 ethylene oxide units in the molecule, a total of from about 0-about 1% by weight of at least one oil, optionally at least one organic solvent, selected from monohydric to tetrahydric $C_2$-$C_6$ alcohols, optionally from about 0.1-about 3% by weight of an anionic surfactant selected from alkyl sulfates, alkyl ether sulfates and ether carboxylic acids with 10 to 20 carbon atoms in the alkyl group and up to 16 glycol ether groups in the molecule, and optionally at least one oxidizing dye precursor, wherein composition (A) has a pH ranging from about 8 to about 11.5, measured at 20° C., wherein all quantitative data being related to the weight of the composition (A). A mixture of the aforementioned oxidizing composition (B) and of the aforementioned composition (A) is prepared. Immediately after preparing the mixture, the ready-to-use composition is deposited on the fibers. The composition is left on the fibers for a period of from about 1 to about 60 minutes, after which the remaining composition is immediately rinsed from the fibers. Optionally, the fibers are dried.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure was to provide an improved oxidizing agent preparation for the oxidative color-changing agent, which is present as a soap-based gel and contains ammonia as an alkalizing agent and optionally contains at least one oxidation dye precursor and has a pH ranging from about 8 to about 11.5 measured at 20° C., with which a homogeneous and viscosity-stable application mixture can be produced, which has a decreased release of ammonia during the whole period of action.

Surprisingly, it was found that aqueous hydrogen peroxide preparations, containing selected 1-alkanols, glycerin fatty acid esters, ethoxylated fatty alcohols, polyols and oils accomplish the task posed in a very good way.

A first object of the present disclosure therefore is an oxidizing composition for the oxidative treatment of hair, containing from about 50-about 96% by weight, preferably from about 70-about 93% by weight particularly from about 80-about 90% by weight of water from about 0.5-20% by weight of hydrogen peroxide, at least one linear, saturated 1-alkanol with 12-30 carbon atoms, preferably in a total amount of from about 2-about 8% by weight and particularly of from about 3 to about 6.5% by weight at least one glyceryl fatty acid ester of the general Formula (1),

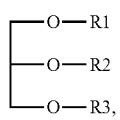
(I)

wherein

R1, R2 and R3 independently of one another represent a hydrogen atom or a group of Formula

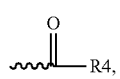
(II)

wherein

R4 represents a linear or branched, saturated or unsaturated $C_{11}$-$C_{27}$ alkyl group with the proviso that at least one at not more than two groups are selected from R1, R2 and R3 for a grouping of Formula (II), wherein the at least one this glyceryl fatty acid ester of the general Formula (I) preferably is contained in a total amount of from about 0.01-about 1% by weight and especially of from about 0.1 to about 8% by weight, at least one ethoxylated fatty alcohol of Formula (III)

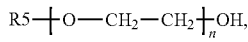
(III)

wherein

R5 represents a linear or branched, saturated or unsaturated $C_{12}$-$C_{28}$ alkyl group, preferably a saturated, linear $C_{16}$ or $C_{18}$ alkyl group and n represents a whole number from 10 to 30, preferably a whole number from 12 to 25 and particularly a whole number from 15 to 20, wherein the at least one ethoxylated fatty alcohol of Formula (III) preferably is contained in an amount of from about 0.25-about 2% by weight and especially of from about 0.5 to about 1.5% by weight, at least one ethoxylated fatty alcohol of Formula (IV)

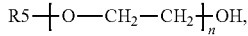
(IV)

wherein

R5 represents a linear or branched, saturated or unsaturated $C_{12}$-$C_{28}$ alkyl group, preferably a saturated, linear $C_{16}$ or $C_{18}$ alkyl group and n represents a whole number from about 50 to about 150, preferably a whole number from about 80 to about 120 and particularly the number 100, wherein the at least one ethoxylated fatty alcohol of Formula (IV) preferably is contained in an amount of from about 0.03-about 0.3% by weight, especially of from about 0.08 to about 0.25% by weight and particularly of from about 0.1-about 0.2% by weight at least one polyol, selected from $C_2$-$C_9$ alkanols with 2-6 hydroxyl groups and polyethylene glycols with 3-20 ethylene oxide units as well as mixtures hereof, preferably is contained in a total amount of from about 1-about 10% by weight, especially of from about 2-about 8% by weight and particularly of from about 3-about 6% by weight at least one oil, preferably is contained in a total amount of from about 0.1-about 5% by weight, particularly of from about 0.2-about 3% by weight and more particularly of from about 0.5-about 2.5% by weight, wherein all quantitative data is related to the weight of the oxidizing composition.

Based on its weight, the oxidizing composition contains from about 50-about 96% by weight, preferably from about 70-about 93% by weight and particularly from about 80-about 90% by weight of water.

Based on its weight, the oxidizing composition contains from about 0.5-about 20% by weight, preferably from about 3-about 12% by weight and particularly from about 6-about 9% by weight. The inventive oxidizing composition contains at least one . . . .

Further oxidizing compositions, preferred as contemplated herein, are exemplified in that at least one linear, saturated 1-alkanol with 12-30 carbon atoms is contained, preferably in a total amount of from about 2-about 8% by weight and especially of from about 3 to about 6.5% by weight, in each case based on the weight of the oxidizing composition.

Preferably, the at least one linear, saturated 1-alkanol with 12-30 carbon atoms is selected from lauryl alcohol, myristyl alcohol, cetyl alcohol, stearyl alcohol, arachidyl alcohol and behenyl alcohol as well as from mixtures of these alcohols, preferably from cetyl alcohol, stearyl alcohol, arachidyl alcohol, behenyl alcohol and cetyl alcohol/stearyl alcohol mixtures.

Preferred oxidizing compositions as contemplated herein in each case contain at least one linear, saturated 1-alkanol with 12-30 carbon atoms in a total amount of from about 2.7-about 6% by weight and preferably of from about 3.0-about 5.0% by weight, wherein at least one 1-alkanol is selected from cetyl alcohol, stearyl alcohol and cetyl alcohol/stearyl alcohol mixtures.

As a fourth, essential formulation constituent, the oxidizing compositions as contemplated herein contain at least one glyceryl fatty acid ester of the general formula (1),

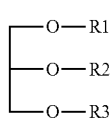
(I)

wherein

R1, R2 and R3 independently of one another represent a hydrogen atom or a group of Formula (II)

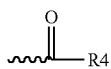
(II)

wherein

R4 represents a linear or branched saturated or unsaturated $C_{11}$-$C_{27}$ alkyl group with the proviso that at least one and not more than two of the groups are selected from R1, R2 and R3 for a group of Formula (II).

The R4 group in the Formula (II) represents a linear or branched, saturated or unsaturated $C_{11}$-$C_{27}$ alkyl group.

Preferably, R4 represents a linear, saturated $C_{11}$-$C_{27}$ alkyl group. Preferably, R4 represents a linear, saturated $C_{13}$-$C_{23}$ alkyl group. Especially, R4 represents a linear, saturated $C_{15}$-$C_{17}$ alkyl group.

Preferred as contemplated herein, the oxidizing compositions are exemplified in that as glyceryl fatty acid esters of the general Formula (I), at least one compound from the group of Formulas (Ia) to (Id) is contained:

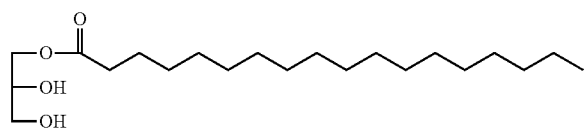
(Ia)

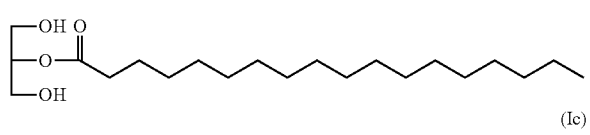
(Ib)

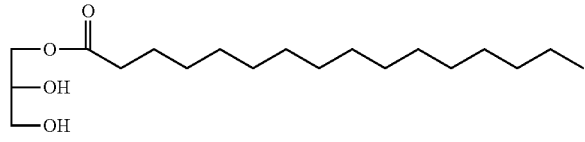
(Ic)

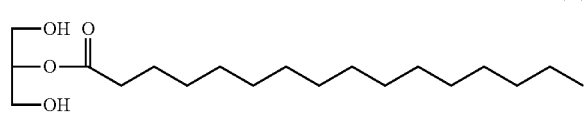
(Id)

The compounds of Formulas (Ia) to (Id) are also known under the name of glyceryl monostearate and glyceryl monopalmitate.

Furthermore preferred as contemplated herein, the oxidizing compositions are exemplified in that as glyceryl fatty acid esters of the general Formula (I), at least one compound from the group of Formulas (Ie) to (Ih) is contained:

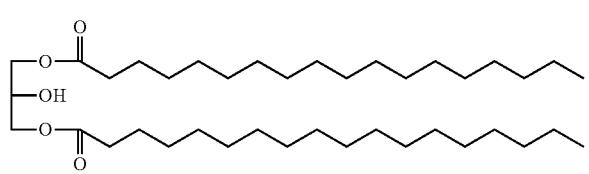
(Ie)

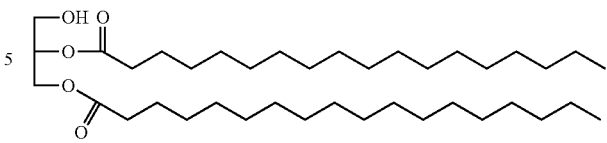
(If)

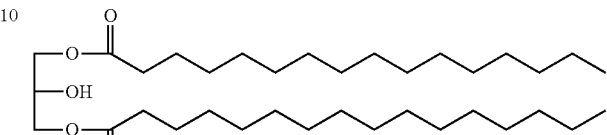
(Ig)

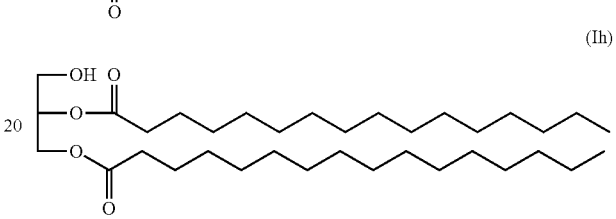
(Ih)

The compounds of Formulas (Ie) to (Ih) are also known under the names of glyceryl distearate and glyceryl dipalmitate.

Furthermore preferred as contemplated herein, the oxidizing compositions are exemplified in that as glyceryl fatty acid esters of the general Formula (I), at least one compound from the group of Formulas (Ia) to (Ih) is contained.

Further oxidizing compositions, particularly preferred as contemplated herein, are exemplified in that as glyceryl fatty acid esters of Formula (I), at least one compound, selected from glyceryl monostearate, glyceryl distearate, glyceryl monopalmitate and glyceryl dipalmitate is contained.

The glyceryl fatty acid esters of Formula (I), in combination with the at least one long chain 1-alkanol, bring about a reduction in the odor of ammonia. The reduction in odor is particularly pronounced if the glyceryl fatty acid ester of Formula (I) and the at least one long-chain 1-alkanol are contained in a particular ratio to one another. For this reason, the glyceryl fatty acid esters of Formula (I) are also preferably contained in certain amounts in the oxidizing composition as contemplated herein.

It is particularly preferred if the oxidizing composition as contemplated herein contains one or more glyceryl fatty esters of Formula (I) in a total amount of from about 0.01-about 1% by weight and especially of from about 0.1 to about 0.8% by weight.

In a further, particularly preferred embodiment, an oxidizing composition as contemplated herein is exemplified in that, as a glyceryl fatty acid ester of Formula (I), at least one compound is selected from glyceryl monostearate, glyceryl distearate, glyceryl monopalmitate and glyceryl dipalmitate in a total amount of from about 0.01 to about 1% by weight and preferably of from about 0.1 to about 0.8% by weight, based on the weight of the oxidizing composition as contemplated herein.

As a fifth, essential formulation component, the oxidizing compositions as contemplated herein contain at least one ethoxylated fatty alcohol of Formula (III),

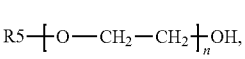
(III)

wherein

R5 represents a saturated or unsaturated, linear or branched, $C_8$-$C_{24}$ alkyl group, preferably a saturated, $C_{16}$ or $C_{18}$ alkyl group and n represents a whole number from 10 to 30, preferably a whole number from 12 to 25 and particularly for a whole number from 15 to 20, wherein the at least one ethoxylated fatty alcohol of Formula (III) preferably is contained in an amount of 0.25-2% by weight and especially of 0.5 to 1.5% by weight.

It is particularly preferred if, as ethoxylated fatty alcohol of Formula (III), it contains one or more ethoxylated fatty alcohol from the group 1-decanol (decyl alcohol), ethoxylated with 10 EO
1-decanol (decyl alcohol), ethoxylated with 11 EO
1-decanol (decyl alcohol), ethoxylated with 12 EO
1-decanol (decyl alcohol), ethoxylated with 13 EO
1-decanol (decyl alcohol), ethoxylated with 14 EO
1-decanol (decyl alcohol), ethoxylated with 15 EO
1-decanol (decyl alcohol), ethoxylated with 16 EO
1-decanol (decyl alcohol), ethoxylated with 17 EO
1-decanol (decyl alcohol), ethoxylated with 18 EO
1-decanol (decyl alcohol), ethoxylated with 19 EO
1-decanol (decyl alcohol), ethoxylated with 20 EO
1-decanol (decyl alcohol), ethoxylated with 21 EO
1-decanol (decyl alcohol), ethoxylated with 22 EO
1-decanol (decyl alcohol), ethoxylated with 23 EO
1-decanol (decyl alcohol), ethoxylated with 24 EO
1-decanol (decyl alcohol), ethoxylated with 25 EO
1-decanol (decyl alcohol), ethoxylated with 26 EO
1-decanol (decyl alcohol), ethoxylated with 27 EO
1-decanol (decyl alcohol), ethoxylated with 28 EO
1-decanol (decyl alcohol), ethoxylated with 29 EO
1-decanol (decyl alcohol), ethoxylated with 30 EO
1-dodecanol (dodecyl alcohol, lauryl alcohol), ethoxylated with 10 EO
1-dodecanol (dodecyl alcohol, lauryl alcohol), ethoxylated with 11 EO
1-dodecanol (dodecyl alcohol, lauryl alcohol), ethoxylated with 12 EO
1-dodecanol (dodecyl alcohol, lauryl alcohol), ethoxylated with 13 EO
1-dodecanol (dodecyl alcohol, lauryl alcohol), ethoxylated with 14 EO
1-dodecanol (dodecyl alcohol, lauryl alcohol), ethoxylated with 15 EO
1-dodecanol (dodecyl alcohol, lauryl alcohol), ethoxylated with 16 EO
1-dodecanol (dodecyl alcohol, lauryl alcohol), ethoxylated with 17 EO
1-dodecanol (dodecyl alcohol, lauryl alcohol), ethoxylated with 18 EO
1-dodecanol (dodecyl alcohol, lauryl alcohol), ethoxylated with 19 EO
1-dodecanol (dodecyl alcohol, lauryl alcohol), ethoxylated with 20 EO
1-dodecanol (dodecyl alcohol, lauryl alcohol), ethoxylated with 21 EO
1-dodecanol (dodecyl alcohol, lauryl alcohol), ethoxylated with 22 EO
1-dodecanol (dodecyl alcohol, lauryl alcohol), ethoxylated with 23 EO
1-dodecanol (dodecyl alcohol, lauryl alcohol), ethoxylated with 24 EO
1-dodecanol (dodecyl alcohol, lauryl alcohol), ethoxylated with 25 EO
1-dodecanol (dodecyl alcohol, lauryl alcohol), ethoxylated with 26 EO
1-dodecanol (dodecyl alcohol, lauryl alcohol), ethoxylated with 27 EO
1-dodecanol (dodecyl alcohol, lauryl alcohol), ethoxylated with 28 EO
1-dodecanol (dodecyl alcohol, lauryl alcohol), ethoxylated with 29 EO
1-dodecanol (dodecyl alcohol, lauryl alcohol), ethoxylated with 30 EO
1-tetradecanol, (tetradecyl alcohol, myristyl alcohol), ethoxylated with 10 EO
1-tetradecanol, (tetradecyl alcohol, myristyl alcohol), ethoxylated with 11 EO
1-tetradecanol, (tetradecyl alcohol, myristyl alcohol), ethoxylated with 12 EO
1-tetradecanol, (tetradecyl alcohol, myristyl alcohol), ethoxylated with 13 EO
1-tetradecanol, (tetradecyl alcohol, myristyl alcohol), ethoxylated with 14 EO
1-tetradecanol, (tetradecyl alcohol, myristyl alcohol), ethoxylated with 15 EO
1-tetradecanol, (tetradecyl alcohol, myristyl alcohol), ethoxylated with 16 EO
1-tetradecanol, (tetradecyl alcohol, myristyl alcohol), ethoxylated with 17 EO
1-tetradecanol, (tetradecyl alcohol, myristyl alcohol), ethoxylated with 18 EO
1-tetradecanol, (tetradecyl alcohol, myristyl alcohol), ethoxylated with 19 EO
1-tetradecanol, (tetradecyl alcohol, myristyl alcohol), ethoxylated with 20 EO
1-tetradecanol, (tetradecyl alcohol, myristyl alcohol), ethoxylated with 21 EO
1-tetradecanol, (tetradecyl alcohol, myristyl alcohol), ethoxylated with 22 EO
1-tetradecanol, (tetradecyl alcohol, myristyl alcohol), ethoxylated with 23 EO
1-tetradecanol, (tetradecyl alcohol, myristyl alcohol), ethoxylated with 24 EO
1-tetradecanol, (tetradecyl alcohol, myristyl alcohol), ethoxylated with 25 EO
1-tetradecanol, (tetradecyl alcohol, myristyl alcohol), ethoxylated with 26 EO
1-tetradecanol, (tetradecyl alcohol, myristyl alcohol), ethoxylated with 27 EO
1-tetradecanol, (tetradecyl alcohol, myristyl alcohol), ethoxylated with 28 EO
1-tetradecanol, (tetradecyl alcohol, myristyl alcohol), ethoxylated with 29 EO
1-tetradecanol, (tetradecyl alcohol, myristyl alcohol), ethoxylated with 30 EO
1-hexadecanol (hexadecyl alcohol, cetyl alcohol, palmityl alcohol), ethoxylated with 10 EO
1-hexadecanol (hexadecyl alcohol, cetyl alcohol, palmityl alcohol), ethoxylated with 11 EO
1-hexadecanol (hexadecyl alcohol, cetyl alcohol, palmityl alcohol), ethoxylated with 12 EO
1-hexadecanol (hexadecyl alcohol, cetyl alcohol, palmityl alcohol), ethoxylated with 13 EO
1-hexadecanol (hexadecyl alcohol, cetyl alcohol, palmityl alcohol), ethoxylated with 14 EO
1-hexadecanol (hexadecyl alcohol, cetyl alcohol, palmityl alcohol), ethoxylated with 15 EO
1-hexadecanol (hexadecyl alcohol, cetyl alcohol, palmityl alcohol), ethoxylated with 16 EO
1-hexadecanol (hexadecyl alcohol, cetyl alcohol, palmityl alcohol), ethoxylated with 17 EO
1-hexadecanol (hexadecyl alcohol, cetyl alcohol, palmityl alcohol), ethoxylated with 18 EO 1-hexadecanol (hexadecyl alcohol, cetyl alcohol, palmityl alcohol), ethoxylated with 19 EO
1-hexadecanol (hexadecyl alcohol, cetyl alcohol, palmityl alcohol), ethoxylated with 20 EO
1-hexadecanol (hexadecyl alcohol, cetyl alcohol, palmityl alcohol), ethoxylated with 21 EO
1-hexadecanol (hexadecyl alcohol, cetyl alcohol, palmityl alcohol), ethoxylated with 22 EO
1-hexadecanol (hexadecyl alcohol, cetyl alcohol, palmityl alcohol), ethoxylated with 23 EO
1-hexadecanol (hexadecyl alcohol, cetyl alcohol, palmityl alcohol), ethoxylated with 24 EO
1-hexadecanol (hexadecyl alcohol, cetyl alcohol, palmityl alcohol), ethoxylated with 25 EO
1-hexadecanol (hexadecyl alcohol, cetyl alcohol, palmityl alcohol), ethoxylated with 26 EO
1-hexadecanol (hexadecyl alcohol, cetyl alcohol, palmityl alcohol), ethoxylated with 27 EO
1-hexadecanol (hexadecyl alcohol, cetyl alcohol, palmityl alcohol), ethoxylated with 28 EO
1-hexadecanol (hexadecyl alcohol, cetyl alcohol, palmityl alcohol), ethoxylated with 29 EO
1-hexadecanol (hexadecyl alcohol, cetyl alcohol, palmityl alcohol), ethoxylated with 30 EO
1-octadecanol (octadecyl alcohol, stearyl alcohol), ethoxylated with 10 EO
1-octadecanol (octadecyl alcohol, stearyl alcohol), ethoxylated with 11 EO
1-octadecanol (octadecyl alcohol, stearyl alcohol), ethoxylated with 12 EO
1-octadecanol (octadecyl alcohol, stearyl alcohol), ethoxylated with 13 EO
1-octadecanol (octadecyl alcohol, stearyl alcohol), ethoxylated with 14 EO
1-octadecanol (octadecyl alcohol, stearyl alcohol), ethoxylated with 15 EO
1-octadecanol (octadecyl alcohol, stearyl alcohol), ethoxylated with 16 EO
1-octadecanol (octadecyl alcohol, stearyl alcohol), ethoxylated with 17 EO
1-octadecanol (octadecyl alcohol, stearyl alcohol), ethoxylated with 18 EO
1-octadecanol (octadecyl alcohol, stearyl alcohol), ethoxylated with 19 EO
1-octadecanol (octadecyl alcohol, stearyl alcohol), ethoxylated with 20 EO
1-octadecanol (octadecyl alcohol, stearyl alcohol), ethoxylated with 21 EO
1-octadecanol (octadecyl alcohol, stearyl alcohol), ethoxylated with 22 EO
1-octadecanol (octadecyl alcohol, stearyl alcohol), ethoxylated with 23 EO
1-octadecanol (octadecyl alcohol, stearyl alcohol), ethoxylated with 24 EO
1-octadecanol (octadecyl alcohol, stearyl alcohol), ethoxylated with 25 EO
1-octadecanol (octadecyl alcohol, stearyl alcohol), ethoxylated with 26 EO
1-octadecanol (octadecyl alcohol, stearyl alcohol), ethoxylated with 27 EO
1-octadecanol (octadecyl alcohol, stearyl alcohol), ethoxylated with 28 EO
1-octadecanol (octadecyl alcohol, stearyl alcohol), ethoxylated with 29 EO
1-octadecanol (octadecyl alcohol, stearyl alcohol), ethoxylated with 30 EO
(9Z)-octadec-9-en-1-ol (oleyl alcohol), ethoxylated with 10 EO
(9Z)-octadec-9-en-1-ol (oleyl alcohol), ethoxylated with 11 EO
(9Z)-octadec-9-en-1-ol (oleyl alcohol), ethoxylated with 12 EO
(9Z)-octadec-9-en-1-ol (oleyl alcohol), ethoxylated with 13 EO
(9Z)-octadec-9-en-1-ol (oleyl alcohol), ethoxylated with 14 EO
(9Z)-octadec-9-en-1-ol (oleyl alcohol), ethoxylated with 15 EO
(9Z)-octadec-9-en-1-ol (oleyl alcohol), ethoxylated with 16 EO
(9Z)-octadec-9-en-1-ol (oleyl alcohol), ethoxylated with 17 EO
(9Z)-octadec-9-en-1-ol (oleyl alcohol), ethoxylated with 18 EO
(9Z)-octadec-9-en-1-ol (oleyl alcohol), ethoxylated with 19 EO
(9Z)-octadec-9-en-1-ol (oleyl alcohol), ethoxylated with 20 EO
(9Z)-octadec-9-en-1-ol (oleyl alcohol), ethoxylated with 21 EO
(9Z)-octadec-9-en-1-ol (oleyl alcohol), ethoxylated with 22 EO
(9Z)-octadec-9-en-1-ol (oleyl alcohol), ethoxylated with 23 EO
(9Z)-octadec-9-en-1-ol (oleyl alcohol), ethoxylated with 24 EO
(9Z)-octadec-9-en-1-ol (oleyl alcohol), ethoxylated with 25 EO
(9Z)-octadec-9-en-1-ol (oleyl alcohol), ethoxylated with 26 EO
(9Z)-octadec-9-en-1-ol (oleyl alcohol), ethoxylated with 27 EO
(9Z)-octadec-9-en-1-ol (oleyl alcohol), ethoxylated with 28 EO
(9Z)-octadec-9-en-1-ol (oleyl alcohol), ethoxylated with 29 EO
(9Z)-octadec-9-en-1-ol (oleyl alcohol), ethoxylated with 30 EO
(9E)-octadec-9-en-1-ol (elaidyl alcohol), ethoxylated with 10 EO
(9E)-octadec-9-en-1-ol (elaidyl alcohol), ethoxylated with 11 EO
(9E)-octadec-9-en-1-ol (elaidyl alcohol), ethoxylated with 12 EO
(9E)-octadec-9-en-1-ol (elaidyl alcohol), ethoxylated with 13 EO
(9E)-octadec-9-en-1-ol (elaidyl alcohol), ethoxylated with 14 EO
(9E)-octadec-9-en-1-ol (elaidyl alcohol), ethoxylated with 15 EO
(9E)-octadec-9-en-1-ol (elaidyl alcohol), ethoxylated with 16 EO
(9E)-octadec-9-en-1-ol (elaidyl alcohol), ethoxylated with 17 EO
(9E)-octadec-9-en-1-ol (elaidyl alcohol), ethoxylated with 18 EO
(9E)-octadec-9-en-1-ol (elaidyl alcohol), ethoxylated with 19 EO
(9E)-octadec-9-en-1-ol (elaidyl alcohol), ethoxylated with 20 EO
(9E)-octadec-9-en-1-ol (elaidyl alcohol), ethoxylated with 21 EO (9E)-octadec-9-en-1-ol (elaidyl alcohol), ethoxylated with 22 EO
(9E)-octadec-9-en-1-ol (elaidyl alcohol), ethoxylated with 23 EO
(9E)-octadec-9-en-1-ol (elaidyl alcohol), ethoxylated with 24 EO
(9E)-octadec-9-en-1-ol (elaidyl alcohol), ethoxylated with 25 EO
(9E)-octadec-9-en-1-ol (elaidyl alcohol), ethoxylated with 26 EO
(9E)-octadec-9-en-1-ol (elaidyl alcohol), ethoxylated with 27 EO
(9E)-octadec-9-en-1-ol (elaidyl alcohol), ethoxylated with 28 EO
(9E)-octadec-9-en-1-ol (elaidyl alcohol), ethoxylated with 29 EO
(9E)-octadec-9-en-1-ol (elaidyl alcohol), ethoxylated with 30 EO
(9Z,12Z)-octadeca-9,12-dien-1-ol (linoleyl alcohol), ethoxylated with 10 EO
(9Z,12Z)-octadeca-9,12-dien-1-ol (linoleyl alcohol), ethoxylated with 11 EO
(9Z,12Z)-octadeca-9,12-dien-1-ol (linoleyl alcohol), ethoxylated with 12 EO
(9Z,12Z)-octadeca-9,12-dien-1-ol (linoleyl alcohol), ethoxylated with 13 EO
(9Z,12Z)-octadeca-9,12-dien-1-ol (linoleyl alcohol), ethoxylated with 14 EO
(9Z,12Z)-octadeca-9,12-dien-1-ol (linoleyl alcohol), ethoxylated with 15 EO
(9Z,12Z)-octadeca-9,12-dien-1-ol (linoleyl alcohol), ethoxylated with 16 EO
(9Z,12Z)-octadeca-9,12-dien-1-ol (linoleyl alcohol), ethoxylated with 17 EO
(9Z,12Z)-octadeca-9,12-dien-1-ol (linoleyl alcohol), ethoxylated with 18 EO
(9Z,12Z)-octadeca-9,12-dien-1-ol (linoleyl alcohol), ethoxylated with 19 EO
(9Z,12Z)-octadeca-9,12-dien-1-ol (linoleyl alcohol), ethoxylated with 20 EO
(9Z,12Z)-octadeca-9,12-dien-1-ol (linoleyl alcohol), ethoxylated with 21 EO
(9Z,12Z)-octadeca-9,12-dien-1-ol (linoleyl alcohol), ethoxylated with 22 EO
(9Z,12Z)-octadeca-9,12-dien-1-ol (linoleyl alcohol), ethoxylated with 23 EO
(9Z,12Z)-octadeca-9,12-dien-1-ol (linoleyl alcohol), ethoxylated with 24 EO
(9Z,12Z)-octadeca-9,12-dien-1-ol (linoleyl alcohol), ethoxylated with 25 EO
(9Z,12Z)-octadeca-9,12-dien-1-ol (linoleyl alcohol), ethoxylated with 26 EO
(9Z,12Z)-octadeca-9,12-dien-1-ol (linoleyl alcohol), ethoxylated with 27 EO
(9Z,12Z)-octadeca-9,12-dien-1-ol (linoleyl alcohol), ethoxylated with 28 EO
(9Z,12Z)-octadeca-9,12-dien-1-ol (linoleyl alcohol), ethoxylated with 29 EO
(9Z,12Z)-octadeca-9,12-dien-1-ol (linoleyl alcohol), ethoxylated with 30 EO
1-eicosanol (eicosyl alcohol, arachyl alcohol), ethoxylated with 10 EO
1-eicosanol (eicosyl alcohol, arachyl alcohol), ethoxylated with 11 EO
1-eicosanol (eicosyl alcohol, arachyl alcohol), ethoxylated with 12 EO
1-eicosanol (eicosyl alcohol, arachyl alcohol), ethoxylated with 13 EO
1-eicosanol (eicosyl alcohol, arachyl alcohol), ethoxylated with 14 EO
1-eicosanol (eicosyl alcohol, arachyl alcohol), ethoxylated with 15 EO
1-eicosanol (eicosyl alcohol, arachyl alcohol), ethoxylated with 16 EO
1-eicosanol (eicosyl alcohol, arachyl alcohol), ethoxylated with 17 EO
1-eicosanol (eicosyl alcohol, arachyl alcohol), ethoxylated with 18 EO
1-eicosanol (eicosyl alcohol, arachyl alcohol), ethoxylated with 19 EO
1-eicosanol (eicosyl alcohol, arachyl alcohol), ethoxylated with 20 EO
1-eicosanol (eicosyl alcohol, arachyl alcohol), ethoxylated with 21 EO
1-eicosanol (eicosyl alcohol, arachyl alcohol), ethoxylated with 22 EO
1-eicosanol (eicosyl alcohol, arachyl alcohol), ethoxylated with 23 EO
1-eicosanol (eicosyl alcohol, arachyl alcohol), ethoxylated with 24 EO
1-eicosanol (eicosyl alcohol, arachyl alcohol), ethoxylated with 25 EO
1-eicosanol (eicosyl alcohol, arachyl alcohol), ethoxylated with 26 EO
1-eicosanol (eicosyl alcohol, arachyl alcohol), ethoxylated with 27 EO
1-eicosanol (eicosyl alcohol, arachyl alcohol), ethoxylated with 28 EO
1-eicosanol (eicosyl alcohol, arachyl alcohol), ethoxylated with 29 EO
1-eicosanol (eicosyl alcohol, arachyl alcohol), ethoxylated with 30 EO
1-docosanol (docosyl alcohol, behenyl alcohol), ethoxylated with 10 EO
1-docosanol (docosyl alcohol, behenyl alcohol), ethoxylated with 11 EO
1-docosanol (docosyl alcohol, behenyl alcohol), ethoxylated with 12 EO
1-docosanol (docosyl alcohol, behenyl alcohol), ethoxylated with 13 EO
1-docosanol (docosyl alcohol, behenyl alcohol), ethoxylated with 14 EO
1-docosanol (docosyl alcohol, behenyl alcohol), ethoxylated with 15 EO
1-docosanol (docosyl alcohol, behenyl alcohol), ethoxylated with 16 EO
1-docosanol (docosyl alcohol, behenyl alcohol), ethoxylated with 17 EO
1-docosanol (docosyl alcohol, behenyl alcohol), ethoxylated with 18 EO
1-docosanol (docosyl alcohol, behenyl alcohol), ethoxylated with 19 EO
1-docosanol (docosyl alcohol, behenyl alcohol), ethoxylated with 20 EO
1-docosanol (docosyl alcohol, behenyl alcohol), ethoxylated with 21 EO
1-docosanol (docosyl alcohol, behenyl alcohol), ethoxylated with 22 EO
1-docosanol (docosyl alcohol, behenyl alcohol), ethoxylated with 23 EO
1-docosanol (docosyl alcohol, behenyl alcohol), ethoxylated with 24 EO 1-docosanol (docosyl alcohol, behenyl alcohol), ethoxylated with 25 EO
1-docosanol (docosyl alcohol, behenyl alcohol), ethoxylated with 26 EO
1-docosanol (docosyl alcohol, behenyl alcohol), ethoxylated with 27 EO
1-docosanol (docosyl alcohol, behenyl alcohol), ethoxylated with 28 EO
1-docosanol (docosyl alcohol, behenyl alcohol), ethoxylated with 29 EO
1-docosanol (docosyl alcohol, behenyl alcohol), ethoxylated with 30 EO as well as mixtures hereof.

Exceptionally preferred are
1-decanol (decyl alcohol), ethoxylated with 10 EO
1-decanol (decyl alcohol), ethoxylated with 20 EO
1-decanol (decyl alcohol), ethoxylated with 30 EO
1-dodecanol (dodecyl alcohol, lauryl alcohol), ethoxylated with 10 EO
1-dodecanol (dodecyl alcohol, lauryl alcohol), ethoxylated with 20 EO
1-dodecanol (dodecyl alcohol, lauryl alcohol), ethoxylated with 30 EO
1-hexadecanol (hexadecyl alcohol, cetyl alcohol, palmityl alcohol), ethoxylated with 10 EO
1-hexadecanol (hexadecyl alcohol, cetyl alcohol, palmityl alcohol), ethoxylated with 12 EO
1-hexadecanol (hexadecyl alcohol, cetyl alcohol, palmityl alcohol), ethoxylated with 15 EO
1-hexadecanol (hexadecyl alcohol, cetyl alcohol, palmityl alcohol), ethoxylated with 20 EO
1-hexadecanol (hexadecyl alcohol, cetyl alcohol, palmityl alcohol), ethoxylated with 25 EO
1-hexadecanol (hexadecyl alcohol, cetyl alcohol, palmityl alcohol), ethoxylated with 30 EO
1-octadecanol (octadecyl alcohol, stearyl alcohol), ethoxylated with 10 EO
1-octadecanol (octadecyl alcohol, stearyl alcohol), ethoxylated with 12 EO
1-octadecanol (octadecyl alcohol, stearyl alcohol), ethoxylated with 15 EO
1-octadecanol (octadecyl alcohol, stearyl alcohol), ethoxylated with 20 EO
1-octadecanol (octadecyl alcohol, stearyl alcohol), ethoxylated with 25 EO
1-octadecanol (octadecyl alcohol, stearyl alcohol), ethoxylated with 30 EO
1-eicosanol (eicosyl alcohol, arachyl alcohol), ethoxylated with 10 EO
1-eicosanol (eicosyl alcohol, arachyl alcohol), ethoxylated with 12 EO
1-eicosanol (eicosyl alcohol, arachyl alcohol), ethoxylated with 15 EO
1-eicosanol (eicosyl alcohol, arachyl alcohol), ethoxylated with 20 EO
1-eicosanol (eicosyl alcohol, arachyl alcohol), ethoxylated with 25 EO
1-eicosanol (eicosyl alcohol, arachyl alcohol), ethoxylated with 30 EO
1-docosanol (docosyl alcohol, behenyl alcohol), ethoxylated with 10 EO
1-docosanol (docosyl alcohol, behenyl alcohol), ethoxylated with 12 EO
1-docosanol (docosyl alcohol, behenyl alcohol), ethoxylated with 15 EO
1-docosanol (docosyl alcohol, behenyl alcohol), ethoxylated with 20 EO
1-docosanol (docosyl alcohol, behenyl alcohol), ethoxylated with 25 EO
1-docosanol (docosyl alcohol, behenyl alcohol), ethoxylated with 30 EO as well as mixtures hereof.

As a sixth, essential formulation component, the oxidizing compositions as contemplated herein contain at least one ethoxylated fatty alcohol of Formula (IV)

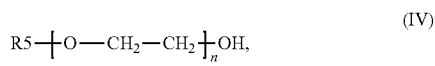

(IV)

$$R5\!\!-\!\!\left[\!O\!-\!CH_2\!-\!CH_2\!\right]_n\!\!OH,$$

wherein

R5 represents a linear or branched, saturated or unsaturated $C_8$-$C_{24}$ alkyl group, preferably a saturated, linear $C_{16}$ or $C_{18}$ alkyl group and n represents a whole number from about 50 to about 150, preferably a whole number from about 80 to about 120 and particularly the number 100, wherein the at least one ethoxylated fatty alcohol of Formula (IV) preferably is contained in a total amount of from about 0.03-about 0.3% by weight, especially of from about 0.08 to about 0.25% by weight and particularly of from about 0.1-about 0.2% by weight.

It is particularly preferred if the ethoxylated fatty alcohol of Formula (IV) contains one or more ethoxylated fatty alcohols from the group comprising 1-dodecanol (dodecyl alcohol, lauryl alcohol), ethoxylated with 50 EO
1-dodecanol (dodecyl alcohol, lauryl alcohol), ethoxylated with 51 EO
1-dodecanol (dodecyl alcohol, lauryl alcohol), ethoxylated with 52 EO
1-dodecanol (dodecyl alcohol, lauryl alcohol), ethoxylated with 53 EO
1-dodecanol (dodecyl alcohol, lauryl alcohol), ethoxylated with 54 EO
1-dodecanol (dodecyl alcohol, lauryl alcohol), ethoxylated with 55 EO
1-dodecanol (dodecyl alcohol, lauryl alcohol), ethoxylated with 56 EO
1-dodecanol (dodecyl alcohol, lauryl alcohol), ethoxylated with 57 EO
1-dodecanol (dodecyl alcohol, lauryl alcohol), ethoxylated with 58 EO
1-dodecanol (dodecyl alcohol, lauryl alcohol), ethoxylated with 59 EO
1-dodecanol (dodecyl alcohol, lauryl alcohol), ethoxylated with 60 EO
1-dodecanol (dodecyl alcohol, lauryl alcohol), ethoxylated with 80 EO
1-dodecanol (dodecyl alcohol, lauryl alcohol), ethoxylated with 81 EO
1-dodecanol (dodecyl alcohol, lauryl alcohol), ethoxylated with 82 EO
1-dodecanol (dodecyl alcohol, lauryl alcohol), ethoxylated with 83 EO
1-dodecanol (dodecyl alcohol, lauryl alcohol), ethoxylated with 84 EO
1-dodecanol (dodecyl alcohol, lauryl alcohol), ethoxylated with 85 EO
1-dodecanol (dodecyl alcohol, lauryl alcohol), ethoxylated with 86 EO
1-dodecanol (dodecyl alcohol, lauryl alcohol), ethoxylated with 87 EO 1-dodecanol (dodecyl alcohol, lauryl alcohol), ethoxylated with 88 EO
1-dodecanol (dodecyl alcohol, lauryl alcohol), ethoxylated with 89 EO
1-dodecanol (dodecyl alcohol, lauryl alcohol), ethoxylated with 90 EO
1-dodecanol (dodecyl alcohol, lauryl alcohol), ethoxylated with 91 EO
1-dodecanol (dodecyl alcohol, lauryl alcohol), ethoxylated with 92 EO
1-dodecanol (dodecyl alcohol, lauryl alcohol), ethoxylated with 93 EO
1-dodecanol (dodecyl alcohol, lauryl alcohol), ethoxylated with 94 EO
1-dodecanol (dodecyl alcohol, lauryl alcohol), ethoxylated with 95 EO
1-dodecanol (dodecyl alcohol, lauryl alcohol), ethoxylated with 96 EO
1-dodecanol (dodecyl alcohol, lauryl alcohol), ethoxylated with 97 EO
1-dodecanol (dodecyl alcohol, lauryl alcohol), ethoxylated with 98 EO
1-dodecanol (dodecyl alcohol, lauryl alcohol), ethoxylated with 99 EO
1-dodecanol (dodecyl alcohol, lauryl alcohol), ethoxylated with 100 EO
1-dodecanol (dodecyl alcohol, lauryl alcohol), ethoxylated with 101 EO
1-dodecanol (dodecyl alcohol, lauryl alcohol), ethoxylated with 102 EO
1-dodecanol (dodecyl alcohol, lauryl alcohol), ethoxylated with 103 EO
1-dodecanol (dodecyl alcohol, lauryl alcohol), ethoxylated with 104 EO
1-dodecanol (dodecyl alcohol, lauryl alcohol), ethoxylated with 105 EO
1-dodecanol (dodecyl alcohol, lauryl alcohol), ethoxylated with 106 EO
1-dodecanol (dodecyl alcohol, lauryl alcohol), ethoxylated with 107 EO
1-dodecanol (dodecyl alcohol, lauryl alcohol), ethoxylated with 108 EO
1-dodecanol (dodecyl alcohol, lauryl alcohol), ethoxylated with 109 EO
1-dodecanol (dodecyl alcohol, lauryl alcohol), ethoxylated with 110 EO
1-dodecanol (dodecyl alcohol, lauryl alcohol), ethoxylated with 111 EO
1-dodecanol (dodecyl alcohol, lauryl alcohol), ethoxylated with 112 EO
1-dodecanol (dodecyl alcohol, lauryl alcohol), ethoxylated with 113 EO
1-dodecanol (dodecyl alcohol, lauryl alcohol), ethoxylated with 114 EO
1-dodecanol (dodecyl alcohol, lauryl alcohol), ethoxylated with 115 EO
1-dodecanol (dodecyl alcohol, lauryl alcohol), ethoxylated with 116 EO
1-dodecanol (dodecyl alcohol, lauryl alcohol), ethoxylated with 117 EO
1-dodecanol (dodecyl alcohol, lauryl alcohol), ethoxylated with 118 EO
1-dodecanol (dodecyl alcohol, lauryl alcohol), ethoxylated with 119 EO
1-dodecanol (dodecyl alcohol, lauryl alcohol), ethoxylated with 120 EO
1-tetradecanol, (tetradecyl alcohol, myristyl alcohol), ethoxylated with 50 EO
1-tetradecanol, (tetradecyl alcohol, myristyl alcohol), ethoxylated with 51 EO
1-tetradecanol, (tetradecyl alcohol, myristyl alcohol), ethoxylated with 52 EO
1-tetradecanol, (tetradecyl alcohol, myristyl alcohol), ethoxylated with 53 EO
1-tetradecanol, (tetradecyl alcohol, myristyl alcohol), ethoxylated with 54 EO
1-tetradecanol, (tetradecyl alcohol, myristyl alcohol), ethoxylated with 55 EO
1-tetradecanol, (tetradecyl alcohol, myristyl alcohol), ethoxylated with 56 EO
1-tetradecanol, (tetradecyl alcohol, myristyl alcohol), ethoxylated with 57 EO
1-tetradecanol, (tetradecyl alcohol, myristyl alcohol), ethoxylated with 58 EO
1-tetradecanol, (tetradecyl alcohol, myristyl alcohol), ethoxylated with 59 EO
1-tetradecanol, (tetradecyl alcohol, myristyl alcohol), ethoxylated with 60 EO
1-tetradecanol, (tetradecyl alcohol, myristyl alcohol), ethoxylated with 80 EO
1-tetradecanol, (tetradecyl alcohol, myristyl alcohol), ethoxylated with 81 EO
1-tetradecanol, (tetradecyl alcohol, myristyl alcohol), ethoxylated with 82 EO
1-tetradecanol, (tetradecyl alcohol, myristyl alcohol), ethoxylated with 83 EO
1-tetradecanol, (tetradecyl alcohol, myristyl alcohol), ethoxylated with 84 EO
1-tetradecanol, (tetradecyl alcohol, myristyl alcohol), ethoxylated with 85 EO
1-tetradecanol, (tetradecyl alcohol, myristyl alcohol), ethoxylated with 86 EO
1-tetradecanol, (tetradecyl alcohol, myristyl alcohol), ethoxylated with 87 EO
1-tetradecanol, (tetradecyl alcohol, myristyl alcohol), ethoxylated with 88 EO
1-tetradecanol, (tetradecyl alcohol, myristyl alcohol), ethoxylated with 89 EO
1-tetradecanol, (tetradecyl alcohol, myristyl alcohol), ethoxylated with 90 EO
1-tetradecanol, (tetradecyl alcohol, myristyl alcohol), ethoxylated with 91 EO
1-tetradecanol, (tetradecyl alcohol, myristyl alcohol), ethoxylated with 92 EO
1-tetradecanol, (tetradecyl alcohol, myristyl alcohol), ethoxylated with 93 EO
1-tetradecanol, (tetradecyl alcohol, myristyl alcohol), ethoxylated with 94 EO
1-tetradecanol, (tetradecyl alcohol, myristyl alcohol), ethoxylated with 95 EO
1-tetradecanol, (tetradecyl alcohol, myristyl alcohol), ethoxylated with 96 EO
1-tetradecanol, (tetradecyl alcohol, myristyl alcohol), ethoxylated with 97 EO
1-tetradecanol, (tetradecyl alcohol, myristyl alcohol), ethoxylated with 98 EO
1-tetradecanol, (tetradecyl alcohol, myristyl alcohol), ethoxylated with 99 EO
1-tetradecanol, (tetradecyl alcohol, myristyl alcohol), ethoxylated with 100 EO
1-tetradecanol, (tetradecyl alcohol, myristyl alcohol), ethoxylated with 101 EO 1-tetradecanol, (tetradecyl alcohol, myristyl alcohol), ethoxylated with 102 EO
1-tetradecanol, (tetradecyl alcohol, myristyl alcohol), ethoxylated with 103 EO
1-tetradecanol, (tetradecyl alcohol, myristyl alcohol), ethoxylated with 104 EO
1-tetradecanol, (tetradecyl alcohol, myristyl alcohol), ethoxylated with 105 EO
1-tetradecanol, (tetradecyl alcohol, myristyl alcohol), ethoxylated with 106 EO
1-tetradecanol, (tetradecyl alcohol, myristyl alcohol), ethoxylated with 107 EO
1-tetradecanol, (tetradecyl alcohol, myristyl alcohol), ethoxylated with 108 EO
1-tetradecanol, (tetradecyl alcohol, myristyl alcohol), ethoxylated with 109 EO
1-tetradecanol, (tetradecyl alcohol, myristyl alcohol), ethoxylated with 110 EO
1-tetradecanol, (tetradecyl alcohol, myristyl alcohol), ethoxylated with 111 EO
1-tetradecanol, (tetradecyl alcohol, myristyl alcohol), ethoxylated with 112 EO
1-tetradecanol, (tetradecyl alcohol, myristyl alcohol), ethoxylated with 113 EO
1-tetradecanol, (tetradecyl alcohol, myristyl alcohol), ethoxylated with 114 EO
1-tetradecanol, (tetradecyl alcohol, myristyl alcohol), ethoxylated with 115 EO
1-tetradecanol, (tetradecyl alcohol, myristyl alcohol), ethoxylated with 116 EO
1-tetradecanol, (tetradecyl alcohol, myristyl alcohol), ethoxylated with 117 EO
1-tetradecanol, (tetradecyl alcohol, myristyl alcohol), ethoxylated with 118 EO
1-tetradecanol, (tetradecyl alcohol, myristyl alcohol), ethoxylated with 119 EO
1-tetradecanol, (tetradecyl alcohol, myristyl alcohol), ethoxylated with 120 EO
1-hexadecanol (hexadecyl alcohol, cetyl alcohol, palmityl alcohol), ethoxylated with 50 EO
1-hexadecanol (hexadecyl alcohol, cetyl alcohol, palmityl alcohol), ethoxylated with 51 EO
1-hexadecanol (hexadecyl alcohol, cetyl alcohol, palmityl alcohol), ethoxylated with 52 EO
1-hexadecanol (hexadecyl alcohol, cetyl alcohol, palmityl alcohol), ethoxylated with 53 EO
1-hexadecanol (hexadecyl alcohol, cetyl alcohol, palmityl alcohol), ethoxylated with 54 EO
1-hexadecanol (hexadecyl alcohol, cetyl alcohol, palmityl alcohol), ethoxylated with 55 EO
1-hexadecanol (hexadecyl alcohol, cetyl alcohol, palmityl alcohol), ethoxylated with 56 EO
1-hexadecanol (hexadecyl alcohol, cetyl alcohol, palmityl alcohol), ethoxylated with 57 EO
1-hexadecanol (hexadecyl alcohol, cetyl alcohol, palmityl alcohol), ethoxylated with 58 EO
1-hexadecanol (hexadecyl alcohol, cetyl alcohol, palmityl alcohol), ethoxylated with 59 EO
1-hexadecanol (hexadecyl alcohol, cetyl alcohol, palmityl alcohol), ethoxylated with 60 EO
1-hexadecanol (hexadecyl alcohol, cetyl alcohol, palmityl alcohol), ethoxylated with 80 EO
1-hexadecanol (hexadecyl alcohol, cetyl alcohol, palmityl alcohol), ethoxylated with 81 EO
1-hexadecanol (hexadecyl alcohol, cetyl alcohol, palmityl alcohol), ethoxylated with 82 EO
1-hexadecanol (hexadecyl alcohol, cetyl alcohol, palmityl alcohol), ethoxylated with 83 EO
1-hexadecanol (hexadecyl alcohol, cetyl alcohol, palmityl alcohol), ethoxylated with 84 EO
1-hexadecanol (hexadecyl alcohol, cetyl alcohol, palmityl alcohol), ethoxylated with 85 EO
1-hexadecanol (hexadecyl alcohol, cetyl alcohol, palmityl alcohol), ethoxylated with 86 EO
1-hexadecanol (hexadecyl alcohol, cetyl alcohol, palmityl alcohol), ethoxylated with 87 EO
1-hexadecanol (hexadecyl alcohol, cetyl alcohol, palmityl alcohol), ethoxylated with 88 EO
1-hexadecanol (hexadecyl alcohol, cetyl alcohol, palmityl alcohol), ethoxylated with 89 EO
1-hexadecanol (hexadecyl alcohol, cetyl alcohol, palmityl alcohol), ethoxylated with 90 EO
1-hexadecanol (hexadecyl alcohol, cetyl alcohol, palmityl alcohol), ethoxylated with 91 EO
1-hexadecanol (hexadecyl alcohol, cetyl alcohol, palmityl alcohol), ethoxylated with 92 EO
1-hexadecanol (hexadecyl alcohol, cetyl alcohol, palmityl alcohol), ethoxylated with 93 EO
1-hexadecanol (hexadecyl alcohol, cetyl alcohol, palmityl alcohol), ethoxylated with 94 EO
1-hexadecanol (hexadecyl alcohol, cetyl alcohol, palmityl alcohol), ethoxylated with 95 EO
1-hexadecanol (hexadecyl alcohol, cetyl alcohol, palmityl alcohol), ethoxylated with 96 EO
1-hexadecanol (hexadecyl alcohol, cetyl alcohol, palmityl alcohol), ethoxylated with 97 EO
1-hexadecanol (hexadecyl alcohol, cetyl alcohol, palmityl alcohol), ethoxylated with 98 EO
1-hexadecanol (hexadecyl alcohol, cetyl alcohol, palmityl alcohol), ethoxylated with 99 EO
1-hexadecanol (hexadecyl alcohol, cetyl alcohol, palmityl alcohol), ethoxylated with 100 EO
1-hexadecanol (hexadecyl alcohol, cetyl alcohol, palmityl alcohol), ethoxylated with 101 EO
1-hexadecanol (hexadecyl alcohol, cetyl alcohol, palmityl alcohol), ethoxylated with 102 EO
1-hexadecanol (hexadecyl alcohol, cetyl alcohol, palmityl alcohol), ethoxylated with 103 EO
1-hexadecanol (hexadecyl alcohol, cetyl alcohol, palmityl alcohol), ethoxylated with 104 EO
1-hexadecanol (hexadecyl alcohol, cetyl alcohol, palmityl alcohol), ethoxylated with 105 EO
1-hexadecanol (hexadecyl alcohol, cetyl alcohol, palmityl alcohol), ethoxylated with 106 EO
1-hexadecanol (hexadecyl alcohol, cetyl alcohol, palmityl alcohol), ethoxylated with 107 EO
1-hexadecanol (hexadecyl alcohol, cetyl alcohol, palmityl alcohol), ethoxylated with 108 EO
1-hexadecanol (hexadecyl alcohol, cetyl alcohol, palmityl alcohol), ethoxylated with 109 EO
1-hexadecanol (hexadecyl alcohol, cetyl alcohol, palmityl alcohol), ethoxylated with 110 EO
1-hexadecanol (hexadecyl alcohol, cetyl alcohol, palmityl alcohol), ethoxylated with 111 EO
1-hexadecanol (hexadecyl alcohol, cetyl alcohol, palmityl alcohol), ethoxylated with 112 EO
1-hexadecanol (hexadecyl alcohol, cetyl alcohol, palmityl alcohol), ethoxylated with 113 EO
1-hexadecanol (hexadecyl alcohol, cetyl alcohol, palmityl alcohol), ethoxylated with 114 EO
1-hexadecanol (hexadecyl alcohol, cetyl alcohol, palmityl alcohol), ethoxylated with 115 EO 1-hexadecanol (hexadecyl alcohol, cetyl alcohol, palmityl alcohol), ethoxylated with 116 EO
1-hexadecanol (hexadecyl alcohol, cetyl alcohol, palmityl alcohol), ethoxylated with 117 EO
1-hexadecanol (hexadecyl alcohol, cetyl alcohol, palmityl alcohol), ethoxylated with 118 EO
1-hexadecanol (hexadecyl alcohol, cetyl alcohol, palmityl alcohol), ethoxylated with 119 EO
1-hexadecanol (hexadecyl alcohol, cetyl alcohol, palmityl alcohol), ethoxylated with 120 EO
1-octadecanol (octadecyl alcohol, stearyl alcohol), ethoxylated with 50 EO
1-octadecanol (octadecyl alcohol, stearyl alcohol), ethoxylated with 51 EO
1-octadecanol (octadecyl alcohol, stearyl alcohol), ethoxylated with 52 EO
1-octadecanol (octadecyl alcohol, stearyl alcohol), ethoxylated with 53 EO
1-octadecanol (octadecyl alcohol, stearyl alcohol), ethoxylated with 54 EO
1-octadecanol (octadecyl alcohol, stearyl alcohol), ethoxylated with 55 EO
1-octadecanol (octadecyl alcohol, stearyl alcohol), ethoxylated with 56 EO
1-octadecanol (octadecyl alcohol, stearyl alcohol), ethoxylated with 57 EO
1-octadecanol (octadecyl alcohol, stearyl alcohol), ethoxylated with 58 EO
1-octadecanol (octadecyl alcohol, stearyl alcohol), ethoxylated with 59 EO
1-octadecanol (octadecyl alcohol, stearyl alcohol), ethoxylated with 60 EO
1-octadecanol (octadecyl alcohol, stearyl alcohol), ethoxylated with 80 EO
1-octadecanol (octadecyl alcohol, stearyl alcohol), ethoxylated with 81 EO
1-octadecanol (octadecyl alcohol, stearyl alcohol), ethoxylated with 82 EO
1-octadecanol (octadecyl alcohol, stearyl alcohol), ethoxylated with 83 EO
1-octadecanol (octadecyl alcohol, stearyl alcohol), ethoxylated with 84 EO
1-octadecanol (octadecyl alcohol, stearyl alcohol), ethoxylated with 85 EO
1-octadecanol (octadecyl alcohol, stearyl alcohol), ethoxylated with 86 EO
1-octadecanol (octadecyl alcohol, stearyl alcohol), ethoxylated with 87 EO
1-octadecanol (octadecyl alcohol, stearyl alcohol), ethoxylated with 88 EO
1-octadecanol (octadecyl alcohol, stearyl alcohol), ethoxylated with 89 EO
1-octadecanol (octadecyl alcohol, stearyl alcohol), ethoxylated with 90 EO
1-octadecanol (octadecyl alcohol, stearyl alcohol), ethoxylated with 91 EO
1-octadecanol (octadecyl alcohol, stearyl alcohol), ethoxylated with 92 EO
1-octadecanol (octadecyl alcohol, stearyl alcohol), ethoxylated with 93 EO
1-octadecanol (octadecyl alcohol, stearyl alcohol), ethoxylated with 94 EO
1-octadecanol (octadecyl alcohol, stearyl alcohol), ethoxylated with 95 EO
1-octadecanol (octadecyl alcohol, stearyl alcohol), ethoxylated with 96 EO
1-octadecanol (octadecyl alcohol, stearyl alcohol), ethoxylated with 97 EO
1-octadecanol (octadecyl alcohol, stearyl alcohol), ethoxylated with 98 EO
1-octadecanol (octadecyl alcohol, stearyl alcohol), ethoxylated with 99 EO
1-octadecanol (octadecyl alcohol, stearyl alcohol), ethoxylated with 100 EO
1-octadecanol (octadecyl alcohol, stearyl alcohol), ethoxylated with 101 EO
1-octadecanol (octadecyl alcohol, stearyl alcohol), ethoxylated with 102 EO
1-octadecanol (octadecyl alcohol, stearyl alcohol), ethoxylated with 103 EO
1-octadecanol (octadecyl alcohol, stearyl alcohol), ethoxylated with 104 EO
1-octadecanol (octadecyl alcohol, stearyl alcohol), ethoxylated with 105 EO
1-octadecanol (octadecyl alcohol, stearyl alcohol), ethoxylated with 106 EO
1-octadecanol (octadecyl alcohol, stearyl alcohol), ethoxylated with 107 EO
1-octadecanol (octadecyl alcohol, stearyl alcohol), ethoxylated with 108 EO
1-octadecanol (octadecyl alcohol, stearyl alcohol), ethoxylated with 109 EO
1-octadecanol (octadecyl alcohol, stearyl alcohol), ethoxylated with 110 EO
1-octadecanol (octadecyl alcohol, stearyl alcohol), ethoxylated with 111 EO
1-octadecanol (octadecyl alcohol, stearyl alcohol), ethoxylated with 112 EO
1-octadecanol (octadecyl alcohol, stearyl alcohol), ethoxylated with 113 EO
1-octadecanol (octadecyl alcohol, stearyl alcohol), ethoxylated with 114 EO
1-octadecanol (octadecyl alcohol, stearyl alcohol), ethoxylated with 115 EO
1-octadecanol (octadecyl alcohol, stearyl alcohol), ethoxylated with 116 EO
1-octadecanol (octadecyl alcohol, stearyl alcohol), ethoxylated with 117 EO
1-octadecanol (octadecyl alcohol, stearyl alcohol), ethoxylated with 118 EO
1-octadecanol (octadecyl alcohol, stearyl alcohol), ethoxylated with 119 EO
1-octadecanol (octadecyl alcohol, stearyl alcohol), ethoxylated with 120 EO
(9Z)-octadec-9-en-1-ol (oleyl alcohol), ethoxylated with 50 EO
(9Z)-octadec-9-en-1-ol (oleyl alcohol), ethoxylated with 51 EO
(9Z)-octadec-9-en-1-ol (oleyl alcohol), ethoxylated with 52 EO
(9Z)-octadec-9-en-1-ol (oleyl alcohol), ethoxylated with 53 EO
(9Z)-octadec-9-en-1-ol (oleyl alcohol), ethoxylated with 54 EO
(9Z)-octadec-9-en-1-ol (oleyl alcohol), ethoxylated with 55 EO
(9Z)-octadec-9-en-1-ol (oleyl alcohol), ethoxylated with 56 EO
(9Z)-octadec-9-en-1-ol (oleyl alcohol), ethoxylated with 57 EO
(9Z)-octadec-9-en-1-ol (oleyl alcohol), ethoxylated with 58 EO (9Z)-octadec-9-en-1-ol (oleyl alcohol), ethoxylated with 59 EO
(9Z)-octadec-9-en-1-ol (oleyl alcohol), ethoxylated with 60 EO
(9Z)-octadec-9-en-1-ol (oleyl alcohol), ethoxylated with 80 EO
(9Z)-octadec-9-en-1-ol (oleyl alcohol), ethoxylated with 81 EO
(9Z)-octadec-9-en-1-ol (oleyl alcohol), ethoxylated with 82 EO
(9Z)-octadec-9-en-1-ol (oleyl alcohol), ethoxylated with 83 EO
(9Z)-octadec-9-en-1-ol (oleyl alcohol), ethoxylated with 84 EO
(9Z)-octadec-9-en-1-ol (oleyl alcohol), ethoxylated with 85 EO
(9Z)-octadec-9-en-1-ol (oleyl alcohol), ethoxylated with 86 EO
(9Z)-octadec-9-en-1-ol (oleyl alcohol), ethoxylated with 87 EO
(9Z)-octadec-9-en-1-ol (oleyl alcohol), ethoxylated with 88 EO
(9Z)-octadec-9-en-1-ol (oleyl alcohol), ethoxylated with 89 EO
(9Z)-octadec-9-en-1-ol (oleyl alcohol), ethoxylated with 90 EO
(9Z)-octadec-9-en-1-ol (oleyl alcohol), ethoxylated with 91 EO
(9Z)-octadec-9-en-1-ol (oleyl alcohol), ethoxylated with 93 EO
(9Z)-octadec-9-en-1-ol (oleyl alcohol), ethoxylated with 94 EO
(9Z)-octadec-9-en-1-ol (oleyl alcohol), ethoxylated with 95 EO
(9Z)-octadec-9-en-1-ol (oleyl alcohol), ethoxylated with 96 EO
(9Z)-octadec-9-en-1-ol (oleyl alcohol), ethoxylated with 97 EO
(9Z)-octadec-9-en-1-ol (oleyl alcohol), ethoxylated with 98 EO
(9Z)-octadec-9-en-1-ol (oleyl alcohol), ethoxylated with 99 EO
(9Z)-octadec-9-en-1-ol (oleyl alcohol), ethoxylated with 99 EO
(9Z)-octadec-9-en-1-ol (oleyl alcohol), ethoxylated with 100 EO
(9Z)-octadec-9-en-1-ol (oleyl alcohol), ethoxylated with 101 EO
(9Z)-octadec-9-en-1-ol (oleyl alcohol), ethoxylated with 102 EO
(9Z)-octadec-9-en-1-ol (oleyl alcohol), ethoxylated with 103 EO
(9Z)-octadec-9-en-1-ol (oleyl alcohol), ethoxylated with 104 EO
(9Z)-octadec-9-en-1-ol (oleyl alcohol), ethoxylated with 105 EO
(9Z)-octadec-9-en-1-ol (oleyl alcohol), ethoxylated with 106 EO
9Z)-octadec-9-en-1-ol (oleyl alcohol), ethoxylated with 107 EO
(9Z)-octadec-9-en-1-ol (oleyl alcohol), ethoxylated with 108 EO
(9Z)-octadec-9-en-1-ol (oleyl alcohol), ethoxylated with 109 EO
(9Z)-octadec-9-en-1-ol (oleyl alcohol), ethoxylated with 110 EO
(9Z)-octadec-9-en-1-ol (oleyl alcohol), ethoxylated with 111 EO
(9Z)-octadec-9-en-1-ol (oleyl alcohol), ethoxylated with 112 EO
(9Z)-octadec-9-en-1-ol (oleyl alcohol), ethoxylated with 113 EO
(9Z)-octadec-9-en-1-ol (oleyl alcohol), ethoxylated with 114 EO
(9Z)-octadec-9-en-1-ol (oleyl alcohol), ethoxylated with 115 EO
(9Z)-octadec-9-en-1-ol (oleyl alcohol), ethoxylated with 116 EO
(9Z)-octadec-9-en-1-ol (oleyl alcohol), ethoxylated with 117 EO
(9Z)-octadec-9-en-1-ol (oleyl alcohol), ethoxylated with 118 EO
(9Z)-octadec-9-en-1-ol (oleyl alcohol), ethoxylated with 119 EO
(9Z)-octadec-9-en-1-ol (oleyl alcohol), ethoxylated with 120 EO
(9E)-octadec-9-en-1-ol (elaidyl alcohol), ethoxylated with 50 EO
(9E)-octadec-9-en-1-ol (elaidyl alcohol), ethoxylated with 51 EO
(9E)-octadec-9-en-1-ol (elaidyl alcohol), ethoxylated with 52 EO
(9E)-octadec-9-en-1-ol (elaidyl alcohol), ethoxylated with 53 EO
(9E)-octadec-9-en-1-ol (elaidyl alcohol), ethoxylated with 54 EO
(9E)-octadec-9-en-1-ol (elaidyl alcohol), ethoxylated with 55 EO
(9E)-octadec-9-en-1-ol (elaidyl alcohol), ethoxylated with 56 EO
(9E)-octadec-9-en-1-ol (elaidyl alcohol), ethoxylated with 57 EO
(9E)-octadec-9-en-1-ol (elaidyl alcohol), ethoxylated with 58 EO
(9E)-octadec-9-en-1-ol (elaidyl alcohol), ethoxylated with 59 EO
(9E)-octadec-9-en-1-ol (elaidyl alcohol), ethoxylated with 60 EO
(9E)-octadec-9-en-1-ol (elaidyl alcohol), ethoxylated with 80 EO
(9E)-octadec-9-en-1-ol (elaidyl alcohol), ethoxylated with 81 EO
(9E)-octadec-9-en-1-ol (elaidyl alcohol), ethoxylated with 82 EO
(9E)-octadec-9-en-1-ol (elaidyl alcohol), ethoxylated with 83 EO
(9E)-octadec-9-en-1-ol (elaidyl alcohol), ethoxylated with 84 EO
(9E)-octadec-9-en-1-ol (elaidyl alcohol), ethoxylated with 85 EO
(9E)-octadec-9-en-1-ol (elaidyl alcohol), ethoxylated with 86 EO
(9E)-octadec-9-en-1-ol (elaidyl alcohol), ethoxylated with 87 EO
(9E)-octadec-9-en-1-ol (elaidyl alcohol), ethoxylated with 88 EO
(9E)-octadec-9-en-1-ol (elaidyl alcohol), ethoxylated with 89 EO
(9E)-octadec-9-en-1-ol (elaidyl alcohol), ethoxylated with 90 EO
(9E)-octadec-9-en-1-ol (elaidyl alcohol), ethoxylated with 91 EO (9E)-octadec-9-en-1-ol (elaidyl alcohol), ethoxylated with 92 EO
(9E)-octadec-9-en-1-ol (elaidyl alcohol), ethoxylated with 93 EO
(9E)-octadec-9-en-1-ol (elaidyl alcohol), ethoxylated with 94 EO
(9E)-octadec-9-en-1-ol (elaidyl alcohol), ethoxylated with 95 EO
(9E)-octadec-9-en-1-ol (elaidyl alcohol), ethoxylated with 96 EO
(9E)-octadec-9-en-1-ol (elaidyl alcohol), ethoxylated with 97 EO
(9E)-octadec-9-en-1-ol (elaidyl alcohol), ethoxylated with 98 EO
(9E)-octadec-9-en-1-ol (elaidyl alcohol), ethoxylated with 99 EO
(9E)-octadec-9-en-1-ol (elaidyl alcohol), ethoxylated with 100 EO
(9E)-octadec-9-en-1-ol (elaidyl alcohol), ethoxylated with 101 EO
(9E)-octadec-9-en-1-ol (elaidyl alcohol), ethoxylated with 102 EO
(9E)-octadec-9-en-1-ol (elaidyl alcohol), ethoxylated with 103 EO
(9E)-octadec-9-en-1-ol (elaidyl alcohol), ethoxylated with 104 EO
(9E)-octadec-9-en-1-ol (elaidyl alcohol), ethoxylated with 105 EO
(9E)-octadec-9-en-1-ol (elaidyl alcohol), ethoxylated with 106 EO
(9E)-octadec-9-en-1-ol (elaidyl alcohol), ethoxylated with 107 EO
(9E)-octadec-9-en-1-ol (elaidyl alcohol), ethoxylated with 108 EO
(9E)-octadec-9-en-1-ol (elaidyl alcohol), ethoxylated with 109 EO
(9E)-octadec-9-en-1-ol (elaidyl alcohol), ethoxylated with 110 EO
(9E)-octadec-9-en-1-ol (elaidyl alcohol), ethoxylated with 111 EO
(9E)-octadec-9-en-1-ol (elaidyl alcohol), ethoxylated with 112 EO
(9E)-octadec-9-en-1-ol (elaidyl alcohol), ethoxylated with 113 EO
(9E)-octadec-9-en-1-ol (elaidyl alcohol), ethoxylated with 114 EO
(9E)-octadec-9-en-1-ol (elaidyl alcohol), ethoxylated with 115 EO
(9E)-octadec-9-en-1-ol (elaidyl alcohol), ethoxylated with 116 EO
(9E)-octadec-9-en-1-ol (elaidyl alcohol), ethoxylated with 117 EO
(9E)-octadec-9-en-1-ol (elaidyl alcohol), ethoxylated with 118 EO
(9E)-octadec-9-en-1-ol (elaidyl alcohol), ethoxylated with 119 EO
(9E)-octadec-9-en-1-ol (elaidyl alcohol), ethoxylated with 120 EO
(9Z,12Z)-octadeca-9,12-dien-1-ol (linoleyl alcohol), ethoxylated with 50 EO
(9Z,12Z)-octadeca-9,12-dien-1-ol (linoleyl alcohol), ethoxylated with 51 EO
(9Z,12Z)-octadeca-9,12-dien-1-ol (linoleyl alcohol), ethoxylated with 52 EO
(9Z,12Z)-octadeca-9,12-dien-1-ol (linoleyl alcohol), ethoxylated with 53 EO
(9Z,12Z)-octadeca-9,12-dien-1-ol (linoleyl alcohol), ethoxylated with 54 EO
(9Z,12Z)-octadeca-9,12-dien-1-ol (linoleyl alcohol), ethoxylated with 55 EO
(9Z,12Z)-octadeca-9,12-dien-1-ol (linoleyl alcohol), ethoxylated with 56 EO
(9Z,12Z)-octadeca-9,12-dien-1-ol (linoleyl alcohol), ethoxylated with 57 EO
(9Z,12Z)-octadeca-9,12-dien-1-ol (linoleyl alcohol), ethoxylated with 58 EO
(9Z,12Z)-octadeca-9,12-dien-1-ol (linoleyl alcohol), ethoxylated with 59 EO
(9Z,12Z)-octadeca-9,12-dien-1-ol (linoleyl alcohol), ethoxylated with 60 EO
(9Z,12Z)-octadeca-9,12-dien-1-ol (linoleyl alcohol), ethoxylated with 80 EO
(9Z,12Z)-octadeca-9,12-dien-1-ol (linoleyl alcohol), ethoxylated with 81 EO
(9Z,12Z)-octadeca-9,12-dien-1-ol (linoleyl alcohol), ethoxylated with 82 EO
(9Z,12Z)-octadeca-9,12-dien-1-ol (linoleyl alcohol), ethoxylated with 83 EO
(9Z,12Z)-octadeca-9,12-dien-1-ol (linoleyl alcohol), ethoxylated with 84 EO
(9Z,12Z)-octadeca-9,12-dien-1-ol (linoleyl alcohol), ethoxylated with 85 EO
(9Z,12Z)-octadeca-9,12-dien-1-ol (linoleyl alcohol), ethoxylated with 86 EO
(9Z,12Z)-octadeca-9,12-dien-1-ol (linoleyl alcohol), ethoxylated with 87 EO
(9Z,12Z)-octadeca-9,12-dien-1-ol (linoleyl alcohol), ethoxylated with 88 EO
(9Z,12Z)-octadeca-9,12-dien-1-ol (linoleyl alcohol), ethoxylated with 89 EO
(9Z,12Z)-octadeca-9,12-dien-1-ol (linoleyl alcohol), ethoxylated with 90 EO
(9Z,12Z)-octadeca-9,12-dien-1-ol (linoleyl alcohol), ethoxylated with 91 EO
(9Z,12Z)-octadeca-9,12-dien-1-ol (linoleyl alcohol), ethoxylated with 92 EO
(9Z,12Z)-octadeca-9,12-dien-1-ol (linoleyl alcohol), ethoxylated with 93 EO
(9Z,12Z)-octadeca-9,12-dien-1-ol (linoleyl alcohol), ethoxylated with 94 EO
(9Z,12Z)-octadeca-9,12-dien-1-ol (linoleyl alcohol), ethoxylated with 95 EO
(9Z,12Z)-octadeca-9,12-dien-1-ol (linoleyl alcohol), ethoxylated with 96 EO
(9Z,12Z)-octadeca-9,12-dien-1-ol (linoleyl alcohol), ethoxylated with 97 EO
(9Z,12Z)-octadeca-9,12-dien-1-ol (linoleyl alcohol), ethoxylated with 98 EO
(9Z,12Z)-octadeca-9,12-dien-1-ol (linoleyl alcohol), ethoxylated with 99 EO
(9Z,12Z)-octadeca-9,12-dien-1-ol (linoleyl alcohol), ethoxylated with 100 EO
(9Z,12Z)-octadeca-9,12-dien-1-ol (linoleyl alcohol), ethoxylated with 101 EO
(9Z,12Z)-octadeca-9,12-dien-1-ol (linoleyl alcohol), ethoxylated with 102 EO
(9Z,12Z)-octadeca-9,12-dien-1-ol (linoleyl alcohol), ethoxylated with 103 EO
(9Z,12Z)-octadeca-9,12-dien-1-ol (linoleyl alcohol), ethoxylated with 104 EO
(9Z,12Z)-octadeca-9,12-dien-1-ol (linoleyl alcohol), ethoxylated with 105 EO (9Z,12Z)-octadeca-9,12-dien-1-ol (linoleyl alcohol), ethoxylated with 106 EO
(9Z,12Z)-octadeca-9,12-dien-1-ol (linoleyl alcohol), ethoxylated with 107 EO
(9Z,12Z)-octadeca-9,12-dien-1-ol (linoleyl alcohol), ethoxylated with 108 EO
(9Z,12Z)-octadeca-9,12-dien-1-ol (linoleyl alcohol), ethoxylated with 110 EO
(9Z,12Z)-octadeca-9,12-dien-1-ol (linoleyl alcohol), ethoxylated with 111 EO
(9Z,12Z)-octadeca-9,12-dien-1-ol (linoleyl alcohol), ethoxylated with 112 EO
(9Z,12Z)-octadeca-9,12-dien-1-ol (linoleyl alcohol), ethoxylated with 113 EO
(9Z,12Z)-octadeca-9,12-dien-1-ol (linoleyl alcohol), ethoxylated with 114 EO
(9Z,12Z)-octadeca-9,12-dien-1-ol (linoleyl alcohol), ethoxylated with 115 EO
(9Z,12Z)-octadeca-9,12-dien-1-ol (linoleyl alcohol), ethoxylated with 116 EO
(9Z,12Z)-octadeca-9,12-dien-1-ol (linoleyl alcohol), ethoxylated with 117 EO
(9Z,12Z)-octadeca-9,12-dien-1-ol (linoleyl alcohol), ethoxylated with 118 EO
(9Z,12Z)-octadeca-9,12-dien-1-ol (linoleyl alcohol), ethoxylated with 119 EO
(9Z,12Z)-octadeca-9,12-dien-1-ol (linoleyl alcohol), ethoxylated with 120 EO
1-eicosanol (eicosyl alcohol, arachyl alcohol), ethoxylated with 50 EO
1-eicosanol (eicosyl alcohol, arachyl alcohol), ethoxylated with 51 EO
1-eicosanol (eicosyl alcohol, arachyl alcohol), ethoxylated with 52 EO
1-eicosanol (eicosyl alcohol, arachyl alcohol), ethoxylated with 53 EO
1-eicosanol (eicosyl alcohol, arachyl alcohol), ethoxylated with 54 EO
1-eicosanol (eicosyl alcohol, arachyl alcohol), ethoxylated with 55 EO
1-eicosanol (eicosyl alcohol, arachyl alcohol), ethoxylated with 56 EO
1-eicosanol (eicosyl alcohol, arachyl alcohol), ethoxylated with 57 EO
1-eicosanol (eicosyl alcohol, arachyl alcohol), ethoxylated with 58 EO
1-eicosanol (eicosyl alcohol, arachyl alcohol), ethoxylated with 59 EO
1-eicosanol (eicosyl alcohol, arachyl alcohol), ethoxylated with 60 EO
1-eicosanol (eicosyl alcohol, arachyl alcohol), ethoxylated with 80 EO
1-eicosanol (eicosyl alcohol, arachyl alcohol), ethoxylated with 81 EO
1-eicosanol (eicosyl alcohol, arachyl alcohol), ethoxylated with 82 EO
1-eicosanol (eicosyl alcohol, arachyl alcohol), ethoxylated with 83 EO
1-eicosanol (eicosyl alcohol, arachyl alcohol), ethoxylated with 84 EO
1-eicosanol (eicosyl alcohol, arachyl alcohol), ethoxylated with 85 EO
1-eicosanol (eicosyl alcohol, arachyl alcohol), ethoxylated with 86 EO
1-eicosanol (eicosyl alcohol, arachyl alcohol), ethoxylated with 87 EO
1-eicosanol (eicosyl alcohol, arachyl alcohol), ethoxylated with 88 EO
1-eicosanol (eicosyl alcohol, arachyl alcohol), ethoxylated with 89 EO
1-eicosanol (eicosyl alcohol, arachyl alcohol), ethoxylated with 90 EO
1-eicosanol (eicosyl alcohol, arachyl alcohol), ethoxylated with 91 EO
1-eicosanol (eicosyl alcohol, arachyl alcohol), ethoxylated with 92 EO
1-eicosanol (eicosyl alcohol, arachyl alcohol), ethoxylated with 93 EO
1-eicosanol (eicosyl alcohol, arachyl alcohol), ethoxylated with 94 EO
1-eicosanol (eicosyl alcohol, arachyl alcohol), ethoxylated with 95 EO
1-eicosanol (eicosyl alcohol, arachyl alcohol), ethoxylated with 96 EO
1-eicosanol (eicosyl alcohol, arachyl alcohol), ethoxylated with 97 EO
1-eicosanol (eicosyl alcohol, arachyl alcohol), ethoxylated with 98 EO
1-eicosanol (eicosyl alcohol, arachyl alcohol), ethoxylated with 99 EO
1-eicosanol (eicosyl alcohol, arachyl alcohol), ethoxylated with 100 EO
1-eicosanol (eicosyl alcohol, arachyl alcohol), ethoxylated with 101 EO
1-eicosanol (eicosyl alcohol, arachyl alcohol), ethoxylated with 102 EO
1-eicosanol (eicosyl alcohol, arachyl alcohol), ethoxylated with 103 EO
1-eicosanol (eicosyl alcohol, arachyl alcohol), ethoxylated with 104 EO
1-eicosanol (eicosyl alcohol, arachyl alcohol), ethoxylated with 105 EO
1-eicosanol (eicosyl alcohol, arachyl alcohol), ethoxylated with 106 EO
1-eicosanol (eicosyl alcohol, arachyl alcohol), ethoxylated with 107 EO
1-eicosanol (eicosyl alcohol, arachyl alcohol), ethoxylated with 108 EO
1-eicosanol (eicosyl alcohol, arachyl alcohol), ethoxylated with 109 EO
1-eicosanol (eicosyl alcohol, arachyl alcohol), ethoxylated with 110 EO
1-eicosanol (eicosyl alcohol, arachyl alcohol), ethoxylated with 111 EO
1-eicosanol (eicosyl alcohol, arachyl alcohol), ethoxylated with 112 EO
1-eicosanol (eicosyl alcohol, arachyl alcohol), ethoxylated with 113 EO
1-eicosanol (eicosyl alcohol, arachyl alcohol), ethoxylated with 114 EO
1-eicosanol (eicosyl alcohol, arachyl alcohol), ethoxylated with 115 EO
1-eicosanol (eicosyl alcohol, arachyl alcohol), ethoxylated with 116 EO
1-eicosanol (eicosyl alcohol, arachyl alcohol), ethoxylated with 117 EO
1-eicosanol (eicosyl alcohol, arachyl alcohol), ethoxylated with 118 EO
1-eicosanol (eicosyl alcohol, arachyl alcohol), ethoxylated with 119 EO
1-eicosanol (eicosyl alcohol, arachyl alcohol), ethoxylated with 120 EO 1-docosanol (docosyl alcohol, behenyl alcohol), ethoxylated with 50 EO
1-docosanol (docosyl alcohol, behenyl alcohol), ethoxylated with 51 EO
1-docosanol (docosyl alcohol, behenyl alcohol), ethoxylated with 52 EO
1-docosanol (docosyl alcohol, behenyl alcohol), ethoxylated with 53 EO
1-docosanol (docosyl alcohol, behenyl alcohol), ethoxylated with 54 EO
1-docosanol (docosyl alcohol, behenyl alcohol), ethoxylated with 55 EO
1-docosanol (docosyl alcohol, behenyl alcohol), ethoxylated with 56 EO
1-docosanol (docosyl alcohol, behenyl alcohol), ethoxylated with 57 EO
1-docosanol (docosyl alcohol, behenyl alcohol), ethoxylated with 58 EO
1-docosanol (docosyl alcohol, behenyl alcohol), ethoxylated with 59 EO
1-docosanol (docosyl alcohol, behenyl alcohol), ethoxylated with 60 EO
1-docosanol (docosyl alcohol, behenyl alcohol), ethoxylated with 80 EO
1-docosanol (docosyl alcohol, behenyl alcohol), ethoxylated with 81 EO
1-docosanol (docosyl alcohol, behenyl alcohol), ethoxylated with 82 EO
1-docosanol (docosyl alcohol, behenyl alcohol), ethoxylated with 83 EO
1-docosanol (docosyl alcohol, behenyl alcohol), ethoxylated with 84 EO
1-docosanol (docosyl alcohol, behenyl alcohol), ethoxylated with 85 EO
1-docosanol (docosyl alcohol, behenyl alcohol), ethoxylated with 86 EO
1-docosanol (docosyl alcohol, behenyl alcohol), ethoxylated with 87 EO
1-docosanol (docosyl alcohol, behenyl alcohol), ethoxylated with 88 EO
1-docosanol (docosyl alcohol, behenyl alcohol), ethoxylated with 89 EO
1-docosanol (docosyl alcohol, behenyl alcohol), ethoxylated with 90 EO
1-docosanol (docosyl alcohol, behenyl alcohol), ethoxylated with 91 EO
1-docosanol (docosyl alcohol, behenyl alcohol), ethoxylated with 92 EO
1-docosanol (docosyl alcohol, behenyl alcohol), ethoxylated with 93 EO
1-docosanol (docosyl alcohol, behenyl alcohol), ethoxylated with 94 EO
1-docosanol (docosyl alcohol, behenyl alcohol), ethoxylated with 95 EO
1-docosanol (docosyl alcohol, behenyl alcohol), ethoxylated with 96 EO
1-docosanol (docosyl alcohol, behenyl alcohol), ethoxylated with 97 EO
1-docosanol (docosyl alcohol, behenyl alcohol), ethoxylated with 98 EO
1-docosanol (docosyl alcohol, behenyl alcohol), ethoxylated with 99 EO
1-docosanol (docosyl alcohol, behenyl alcohol), ethoxylated with 100 EO
1-docosanol (docosyl alcohol, behenyl alcohol), ethoxylated with 101 EO
1-docosanol (docosyl alcohol, behenyl alcohol), ethoxylated with 102 EO
1-docosanol (docosyl alcohol, behenyl alcohol), ethoxylated with 103 EO
1-docosanol (docosyl alcohol, behenyl alcohol), ethoxylated with 104 EO
1-docosanol (docosyl alcohol, behenyl alcohol), ethoxylated with 105 EO
1-docosanol (docosyl alcohol, behenyl alcohol), ethoxylated with 106 EO
1-docosanol (docosyl alcohol, behenyl alcohol), ethoxylated with 107 EO
1-docosanol (docosyl alcohol, behenyl alcohol), ethoxylated with 108 EO
1-docosanol (docosyl alcohol, behenyl alcohol), ethoxylated with 109 EO
1-docosanol (docosyl alcohol, behenyl alcohol), ethoxylated with 110 EO
1-docosanol (docosyl alcohol, behenyl alcohol), ethoxylated with 111 EO
1-docosanol (docosyl alcohol, behenyl alcohol), ethoxylated with 112 EO
1-docosanol (docosyl alcohol, behenyl alcohol), ethoxylated with 113 EO
1-docosanol (docosyl alcohol, behenyl alcohol), ethoxylated with 114 EO
1-docosanol (docosyl alcohol, behenyl alcohol), ethoxylated with 115 EO
1-docosanol (docosyl alcohol, behenyl alcohol), ethoxylated with 116 EO
1-docosanol (docosyl alcohol, behenyl alcohol), ethoxylated with 117 EO
1-docosanol (docosyl alcohol, behenyl alcohol), ethoxylated with 118 EO
1-docosanol (docosyl alcohol, behenyl alcohol), ethoxylated with 119 EO
1-docosanol (docosyl alcohol, behenyl alcohol), ethoxylated with 120 EO A quite particularly advantageous, oxidizing composition as contemplated herein for dyeing and/or brightening keratinic fibers is exemplified in that they, as ethoxylated fatty alcohol(s) of Formula (IV), they contain one or more compounds of the group comprising:

1-hexadecanol (hexadecyl alcohol, cetyl alcohol, palmityl alcohol), ethoxylated with 50 EO
1-hexadecanol (hexadecyl alcohol, cetyl alcohol, palmityl alcohol), ethoxylated with 51 EO
1-hexadecanol (hexadecyl alcohol, cetyl alcohol, palmityl alcohol), ethoxylated with 52 EO
1-hexadecanol (hexadecyl alcohol, cetyl alcohol, palmityl alcohol), ethoxylated with 53 EO
1-hexadecanol (hexadecyl alcohol, cetyl alcohol, palmityl alcohol), ethoxylated with 54 EO
1-hexadecanol (hexadecyl alcohol, cetyl alcohol, palmityl alcohol), ethoxylated with 55 EO
1-hexadecanol (hexadecyl alcohol, cetyl alcohol, palmityl alcohol), ethoxylated with 56 EO
1-hexadecanol (hexadecyl alcohol, cetyl alcohol, palmityl alcohol), ethoxylated with 57 EO
1-hexadecanol (hexadecyl alcohol, cetyl alcohol, palmityl alcohol), ethoxylated with 58 EO
1-hexadecanol (hexadecyl alcohol, cetyl alcohol, palmityl alcohol), ethoxylated with 59 EO
1-hexadecanol (hexadecyl alcohol, cetyl alcohol, palmityl alcohol), ethoxylated with 60 EO
1-hexadecanol (hexadecyl alcohol, cetyl alcohol, palmityl alcohol), ethoxylated with 90 EO 1-hexadecanol (hexadecyl alcohol, cetyl alcohol, palmityl alcohol), ethoxylated with 91 EO
1-hexadecanol (hexadecyl alcohol, cetyl alcohol, palmityl alcohol), ethoxylated with 92 EO
1-hexadecanol (hexadecyl alcohol, cetyl alcohol, palmityl alcohol), ethoxylated with 93 EO
1-hexadecanol (hexadecyl alcohol, cetyl alcohol, palmityl alcohol), ethoxylated with 94 EO
1-hexadecanol (hexadecyl alcohol, cetyl alcohol, palmityl alcohol), ethoxylated with 95 EO
1-hexadecanol (hexadecyl alcohol, cetyl alcohol, palmityl alcohol), ethoxylated with 96 EO
1-hexadecanol (hexadecyl alcohol, cetyl alcohol, palmityl alcohol), ethoxylated with 97 EO
1-hexadecanol (hexadecyl alcohol, cetyl alcohol, palmityl alcohol), ethoxylated with 98 EO
1-hexadecanol (hexadecyl alcohol, cetyl alcohol, palmityl alcohol), ethoxylated with 99 EO
1-hexadecanol (hexadecyl alcohol, cetyl alcohol, palmityl alcohol), ethoxylated with 100 EO
1-hexadecanol (hexadecyl alcohol, cetyl alcohol, palmityl alcohol), ethoxylated with 101 EO
1-hexadecanol (hexadecyl alcohol, cetyl alcohol, palmityl alcohol), ethoxylated with 102 EO
1-hexadecanol (hexadecyl alcohol, cetyl alcohol, palmityl alcohol), ethoxylated with 103 EO
1-hexadecanol (hexadecyl alcohol, cetyl alcohol, palmityl alcohol), ethoxylated with 104 EO
1-hexadecanol (hexadecyl alcohol, cetyl alcohol, palmityl alcohol), ethoxylated with 105 EO
1-hexadecanol (hexadecyl alcohol, cetyl alcohol, palmityl alcohol), ethoxylated with 106 EO
1-hexadecanol (hexadecyl alcohol, cetyl alcohol, palmityl alcohol), ethoxylated with 107 EO
1-hexadecanol (hexadecyl alcohol, cetyl alcohol, palmityl alcohol), ethoxylated with 108 EO
1-hexadecanol (hexadecyl alcohol, cetyl alcohol, palmityl alcohol), ethoxylated with 109 EO
1-hexadecanol (hexadecyl alcohol, cetyl alcohol, palmityl alcohol), ethoxylated with 110 EO
1-octadecanol (octadecyl alcohol, stearyl alcohol), ethoxylated with 50 EO
1-octadecanol (octadecyl alcohol, stearyl alcohol), ethoxylated with 51 EO
1-octadecanol (octadecyl alcohol, stearyl alcohol), ethoxylated with 52 EO
1-octadecanol (octadecyl alcohol, stearyl alcohol), ethoxylated with 53 EO
1-octadecanol (octadecyl alcohol, stearyl alcohol), ethoxylated with 54 EO
1-octadecanol (octadecyl alcohol, stearyl alcohol), ethoxylated with 55 EO
1-octadecanol (octadecyl alcohol, stearyl alcohol), ethoxylated with 56 EO
1-octadecanol (octadecyl alcohol, stearyl alcohol), ethoxylated with 57 EO
1-octadecanol (octadecyl alcohol, stearyl alcohol), ethoxylated with 58 EO
1-octadecanol (octadecyl alcohol, stearyl alcohol), ethoxylated with 59 EO
1-octadecanol (octadecyl alcohol, stearyl alcohol), ethoxylated with 60 EO
1-octadecanol (octadecyl alcohol, stearyl alcohol), ethoxylated with 90 EO
1-octadecanol (octadecyl alcohol, stearyl alcohol), ethoxylated with 91 EO
1-octadecanol (octadecyl alcohol, stearyl alcohol), ethoxylated with 92 EO
1-octadecanol (octadecyl alcohol, stearyl alcohol), ethoxylated with 93 EO
1-octadecanol (octadecyl alcohol, stearyl alcohol), ethoxylated with 94 EO
1-octadecanol (octadecyl alcohol, stearyl alcohol), ethoxylated with 95 EO
1-octadecanol (octadecyl alcohol, stearyl alcohol), ethoxylated with 96 EO
1-octadecanol (octadecyl alcohol, stearyl alcohol), ethoxylated with 97 EO
1-octadecanol (octadecyl alcohol, stearyl alcohol), ethoxylated with 98 EO
1-octadecanol (octadecyl alcohol, stearyl alcohol), ethoxylated with 99 EO
1-octadecanol (octadecyl alcohol, stearyl alcohol), ethoxylated with 100 EO
1-octadecanol (octadecyl alcohol, stearyl alcohol), ethoxylated with 101 EO
1-octadecanol (octadecyl alcohol, stearyl alcohol), ethoxylated with 102 EO
1-octadecanol (octadecyl alcohol, stearyl alcohol), ethoxylated with 103 EO
1-octadecanol (octadecyl alcohol, stearyl alcohol), ethoxylated with 104 EO
1-octadecanol (octadecyl alcohol, stearyl alcohol), ethoxylated with 105 EO
1-octadecanol (octadecyl alcohol, stearyl alcohol), ethoxylated with 106 EO
1-octadecanol (octadecyl alcohol, stearyl alcohol), ethoxylated with 107 EO
1-octadecanol (octadecyl alcohol, stearyl alcohol), ethoxylated with 108 EO
1-octadecanol (octadecyl alcohol, stearyl alcohol), ethoxylated with 109 EO
1-octadecanol (octadecyl alcohol, stearyl alcohol), ethoxylated with 110 EO.

As seventh essential formulation constituent, the oxidation compositions as contemplated herein contain at least one polyol, selected from $C_2$-$C_9$ alkanols with 2-6 hydroxyl groups and polyethylene glycols with 3-20 ethylene oxide units as well as mixtures hereof, preferably in a total amount of from about 1-about 10% by weight, especially of from about 2-about 8% by weight and particularly of about 3-about 6% by weight.

$C_2$-$C_9$ alkanols with 2-6 hydroxyl groups and/or polyethylene glycols with 3-20 ethylene oxide units, preferred as contemplated herein, selected from 1,2-propylene glycol, glycerin, butylene glycols such as 1,2-butylene glycol, 1,3-butylene glycol and 1,4-butylene glycol, pentylene glycols such as 1,2-pentanediol and 1,5-pentanediol, hexanediols such as 1,6-hexanediol and 2-methyl-1,3-propanediol (INCI: hexylene glycol), hexanetrioils such as 1,2,6-hexanetriol, 1,2-octanediol, 1,8-octanediol, dipropylene glycol tripropylene glycol, diglycerin, triglycerin, erythritol, sorbitol and mixtures of the aforementioned substances Suitable, water-soluble polyethylene glycols are selected from PEG-3, PEG-4, PEG-6, PEG-7, PEG-8, PEG-9, PEG-10, PEG-12, PEG-14, PEG-16, PEG-18 and PEG-20, as well as mixtures hereof, PEG-3 to PEG-8 being preferred.

As eighth essential formulation constituent, the oxidizing compositions as contemplated herein contain at least one oil. Preferably, the at least one oil is contained in a total amount of from about 0.1-about 5% by weight, especially of from about 0.2-about 3% by weight and particularly of from about 0.5-about 2.5% by weight, in each case based on the weight of the oxidizing composition.

Oils, which are preferred as contemplated herein, are selected from natural and synthetic hydrocarbons, especially from mineral oils, paraffin oils, $C_{18}$-$C_{30}$ iso-paraffins, especially isoeicosan, poly-iso-butenes and polydecenes, which may be obtained under the names of Emery® 3004, 3006 and 3010 or under the name of Ethylflo® from Albemarle or of Nexbase® 2004G from Nestle, and are furthermore selected from $C_8$-$C_{16}$ iso-paraffins, especially from isodecane, isododecane, isotetradecane and isohexadecane as well as mixtures hereof, such as 1,3-di-(2-ethylhexyl)-cyclohexane (obtainable under the commercial name of Cetiol® S from BASF).

Further oils, preferred as contemplated herein, are selected from benzoate esters of linear or branched $C_8$-$C_{22}$ alkanols. Especially preferred are $C_{12}$-$C_{15}$ alkyl benzoates, obtainable, for example, as a commercial product Finsolv® TN, isostearyl benzoate, obtainable, for example, as the commercial product Finsolv® SB, ethylhexyl benzoate, obtainable, for example, as the commercial product Finsolv® EB and octyldodecyl benzoate, obtainable, for example, as the commercial product Finsolv® BOD.

Further oils, which are preferred as contemplated herein, are selected from fatty alcohols with 6-30 carbon atoms, which are unsaturated or branched and saturated or branched and unsaturated. The branched alcohols frequently are also referred to as Guerbet alcohols, since they can be obtained by the Guerbet reaction. 2-Hexyldecanol (Eutanol® G 16), 2-octyldecanol Eutanol® G), 2-ethylhexyl alcohol and iso-stearyl alcohol are preferred alcohols.

Further preferred oils are selected from mixtures of Guerbert alcohols and Guerbert esters, such as the commercial product, Cetiol® PGL (2-hexyldecanol and 2-hexyldecyl laurate).

Further cosmetic oils, preferred as contemplated herein, are selected from the triglycerides (=triple esters of glycerol) of linear or branched, saturated or unsaturated, optionally hydroxylated $C_8$-$_{30}$ fatty acids. Particularly preferred is the use of natural oils, such as Amaranths seed oil, apricot kernel oil, argan oil, avocado oil, babassu oil, cottonseed oil, borage seed oil, camelina oil, thistle oil, peanut oil, pomegranate seeds, grapefruit seed oil, hemp oil, hazelnut oil, elderberry seed oil, currant seed oil, jojoba oil, seed oil, macadamia nut oil, corn oil, almond oil, marula oil, evening primrose oil, olive oil, palm oil, palm kernel oil, Brasil nut oil, pecan nut oil, peach kernel oil, rapeseed oil, castor oil, seabuckthorn berry oil, seabuckthorn kernel oil, sesame oil, soybean oil, sunflower oil, grape nut oil, walnut oil, rosehip seed oil, wheat germ oil and the volatile portions of coconut oil and the like. However, synthetic triglycerides oils, in particular capric/caprylic triglycerides, for example the commercial products Myritol® 318, Myritol® 331 (BASF) or Miglyol® 812 (Hues) with linear fatty esters and glyceryl triisostearin with branched fatty esters, are also preferred.

Further cosmetic oils, which are particularly preferred as contemplated herein, are dicarboxylate esters of linear or branched $C_2$-$C_{10}$ alkanols, in particular diisopropyl adipate, di-n-butyl adipate, di-(2-ethylhexyl) adipate, dioctyl adipate, diethyl/di-n-butyl/dioctyl sebacate, diisopropyl sebacate, dioctyl maleate, dioctyl maleate, dicaprylyl maleate, diisooctyl succinate, di-2-ethylhexyl succinate and di-(2-hexyldecyl) succinate.

Further cosmetic oils, particularly preferred as contemplated herein, are selected from the esters of linear or branched, saturated or unsaturated fatty alcohols with 2-30 carbon atoms with linear or branched, saturated or unsaturated fatty acids having 2-30 carbon atoms, which may be hydroxylated. These include 2-hexyldecyl stearate (Eutanol® G 16 S), 2-hexyldecyl laurate, isodecyl neopentanoate, isononyl isononanoate, 2-ethylhexyl palmitate (Cegesoft® C 24) and 2-ethylhexyl stearate (Cetiol® 868). Likewise preferred are Isopropyl myristate, isopropyl palmitate, isopropyl stearate, isopropyl isostearate, isopropyl oleate, isooctyl stearate, isononyl stearate, isocetyl stearate isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyl octanoic acid-2-butyl octanoate, diisotridecyl acetate, n-butyl stearate, n-hexyl laurate, n-decyl oleate, oleyl oleate, oleyl erucate, erucyl oleate, erucyl erucae, ethylene glycol dioleate and ethylene glycol dipalmitate.

Further cosmetic oils preferred as contemplated herein, are selected from the addition products of from about 1 to about 5 propylene oxide units and monohydric or polyhydric $C_8$-$_{22}$ alkanols, such as octanol, decanol, decanediol, lauryl alcohol, myristyl alcohol and stearyl alcohol, such as PPG-2 myristyl ether and PPG-3 myristyl ether (Witconol® APM).

Further cosmetic oils, preferred as contemplated herein, are selected from the addition products of at least 6 ethylene oxide units and/or propylene oxide units and monohydric or polyhydric $C_{3-22}$ alkanols such as glycerol, butanol, butanediol, myristyl alcohol and stearyl alcohol, which may be esterified if desired, such as PPG-14-butyl ether (Ucon Fluid® AP), PPG-9-butyl ether (Breox® B25), PPG-10 butanediol (Macol® 57), PPG-15 stearyl ether (Arlamol® E) and glycereth-7-diiso-nonanoate.

Further cosmetic oils, preferred as contemplated herein, are selected from the $C_8$-$C_{22}$ fatty alcohol esters of monohydric or polyhydric $C_2$-$C_7$ hydroxycarboxylic acids, in particular the esters of glycolic acid, lactic acid, malic acid, tartaric acid, citric acid and salicylic acid. Such esters based on linear $C_{14/15}$ alkanols, such as $C_{12}$-$C_{15}$ alkyl lactate, and $C_{12/13}$ alkanols branched in the 2-position, are obtainable under the trademark of Cosmacol® from Nordmann, Rassmann GmbH & Co, Hamburg, in particular the commercial products Cosmacol® EMI, Cosmacol® ESI and Cosmacol® ETI.

Further cosmetic oils, preferred as contemplated herein, are selected from the symmetrical, asymmetrical or cyclic esters of carbonic acids with $C_{3-22}$ alkanols, $C_{3-22}$ alkanediols or $C_{3-22}$ alkanetriols, for example dicaprylyl carbonate (Cetiol® CC) or the esters of the teaching of DE 19756454 A1, especially glycerin carbonate.

Further cosmetic oils, which may be preferred as contemplated herein, are selected from the esters of dimers of unsaturated $C_{12}$-$C_{22}$ fatty acids (dimer fatty acids) with monohydric linear, branched or cyclic $C_2$-$C_{18}$ alkanols or with polyhydric linear or branched $C_2$-$C_6$ alkanols.

Further cosmetic oils, which are suitable as contemplated herein, are selected from the silicone oils, for example dialkyl- and alkylarylsiloxanes, such as cyclopentasiloxane, cyclohexasiloxane, dimethylpolysiloxane and methylphenylpolysiloxane, but also hexamethyldisiloxane, octamethyl-trisiloxane and decamethyltetrasiloxane. Volatile silicone oils, which may be cyclic, such as octamethylcyclotetrasiloxane, decamethylcyclopentasiloxane, and dodecamethylcyclohexa-siloxane, and mixtures thereof, such as are present, for example, in Dow Corning's DC 244, 245, 344 and 345 commercial products may be preferred. Likewise suitable are volatile, linear especially hexamethyldisiloxane ($L_2$), octylmethyltrisiloxane ($L_3$), decamethyltrisiloxane ($L_4$) and mixtures of two and three of $L_2$, $L_3$ and/or $L_4$, preferably such mixtures, which are contained, for example, in the commercial products DC 2-1184, Dow Corning® 200 (0.65 cSt) and Dow Corning® 200 (1.5 cSt), being preferred. Preferred non-volatile silicone oils are selected from higher molecular weight linear dimethylpolysiloxanes. Commercially available, for example, under the designation of Dow Corning®. 190, Dow Corning® 200 fluid with kinematic viscosities (25° C.) in the range of 5-100 cSt, preferably 5-50 cSt or also 5-10 cSt, and dimethylpolysiloxane with a kinematic viscosity (25° C.) of about 350 cSt.

It may be exceptionally preferred if mixtures of the aforementioned oils are used.

Preferred, oxidizing compositions as contemplated herein are exemplified in that the cosmetic oil is selected from natural and synthetic hydrocarbons, particularly preferred from paraffin oils, $C_{18}$-$C_{30}$ iso-paraffins, especially from isoeicosan, polyisobutene and polydecene, $C_8$-$C_{16}$ isoparaffins, as well as from 1,3-di-(2-ethylhexyl)-cyclohexane; the benzoates esters of linear or branched $C_{8-22}$ alkanols, fatty alcohols with 6-30 carbon atoms, which are unsaturated or branched and saturated or branched and unsaturated; triglycerides of linear or branched, saturated or unsaturated, optionally hydroxylated $C_{8-30}$ fatty acids, especially natural oils; the dicarboxylate esters of linear or branched $C_2$-$C_{10}$ alkanols, the esters of linear or branched, saturated or unsaturated fatty alcohols with 2-30 carbon atoms with linear or branched, saturated or unsaturated fatty acids with 2-30 carbon atoms, which may be hydroxylated; the addition products of 1 to 5 propylene oxide units and monohydric or multi-hydric $C_{8-22}$ alkanols; the addition products of at least 6 ethylene oxide units and/or propylene oxide units and monohydric or multihydric $C_{3-22}$ alkanols; the $C_8$-$C_{22}$ fatty alcohol esters of monohydric or multi-hydric $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanetriols; the esters of dimers of unsaturated $C_{12}$-$C_{22}$ fatty acids (dimer fatty acids) with monohydric linear, branched or cyclic $C_2$-$C_{18}$ alkanols or with polyhydric linear or branched $C_2$-$C_6$ alkanols; silicones and mixtures of the abovementioned substances.

Oxidation compositions, particularly preferred as contemplated herein, are exemplified in that at least one lamellar phase is contained. The constituents of the oxidation compositions as contemplated herein preferably form at least one lamellar phase, preferably an L beta phase, which, when mixed with an ammonia-containing alkalizing composition, preferably when mixed with the soap gel-based alkalizing composition, used as contemplated herein, causes the ammonia, dissolved in the water phase, to remain bound in the water of the lamellar phases and thus reduces the evaporation of the ammonia. The oxidizing composition as contemplated herein preferably has a viscosity ranging from about 800-about 3500 mPas and particularly from about 1500-about 3000 mPas, measured in each case at 20° C. in the Type MV2 Haake viscosimeter at a speed of 8 RPM.

For stabilizing the oxidizing composition during storage, it is particularly preferred that the oxidizing composition as contemplated herein has an acidic pH, especially a pH ranging from about 2.5 to about 5.5 and preferably from about 3.0 to about o 5.0. Preferred acidifying agents are food acids, such as citric acid, acetic acid, malic acid or tartaric acid, and dilute mineral acids, especially phosphoric acid.

Preferably, a complexing agent is used to stabilize the oxidizing agent in the oxidizing composition as contemplated herein. Complexing agents are materials, which can complex metallic ions. Preferred complexing agents are the so-called chelate complexing agents, that is, materials which can form cyclic compounds with metal ions, wherein an individual ligand may occupy more than one coordination site at a central atom. The number of ligands bound depends on the coordination number of the central ions. Conventional chelate complexing agents, preferred within the scope of the present disclosure, are, for example, polyoloxycarboxylic acids, polyamines, ethylenediaminetetraacetic acid (EDTA), nitriloacetic acid (NTA) and hydroxyethanediphosphonic acids or the alkali salts thereof. Complexing agents, preferred as contemplated herein, are phosphonates, preferably hydroxy alkane phosphonates or aminoalkane phosphonates and in particular 1-hydroxyethane 1,1-diphosphonate (HEDP) or its di- or tetrasodium salt and/or ethylenediaminetetramethylene phosphate (EDTMP) or its hexasodium salt and/or diethylenetriaminepentamethylene phosphate (DTPMP) or its hepta- or octasodium salt. Dipicolinic is also preferred as contemplated herein as a complexing agent. Compositions, which contain a combination of EDTA salt and HEDP and dipicolinic acid are particularly preferred as contemplated herein.

A further subject matter of the present disclosure is a kit for oxidatively changing the color of keratinic fibers, containing two compositions (A) and (B) separately from one another, wherein composition (B) contains an oxidizing composition, as described above, that is, an oxidizing composition containing from about 50-about 96% by weight, preferably from about 70-about 93% by weight particularly from about 80-about 90% by weight of water from about 0.5-about 20% by weight of hydrogen peroxide, at least one linear, saturated 1-alkanol with 12-30 carbon atoms, preferably in a total amount of from about 2-about 8% by weight and particularly of from about 3-about 6.5% by weight at least one glyceryl fatty acid ester of the general Formula (1),

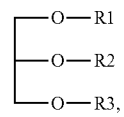

(I)

wherein
R1, R2 and R3 independently of one another represent a hydrogen atom or a group of Formula (II)

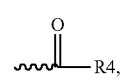

(II)

wherein
R4 represents a linear or branched, saturated or unsaturated $C_{11}$-$C_{27}$ alkyl group with the proviso that at least one at not more than two groups are selected from R1, R2 and R3 for a grouping of Formula (II), wherein the at least one glyceryl fatty acid ester of the general Formula (I) preferably is contained in a total amount of from about 0.01-about 1% by weight and especially of from about 0.1 to about 8% by weight, at least one ethoxylated fatty alcohol of Formula (III)

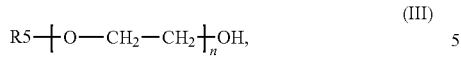

wherein

R5 represents a linear or branched, saturated or unsaturated $C_8$-$C_{24}$ alkyl group, preferably a saturated, linear $C_{16}$ or $C_{18}$ alkyl group and n represents a whole number from 10 to 30, preferably a whole number from 12 to 25, furthermore preferably a whole number from 15 to 20, wherein the at least one ethoxylated fatty alcohol of Formula (III) preferably is contained in an amount of from about 0.25-about 2% by weight and especially of from about 0.5 to about 1.5% by weight.

at least one ethoxylated fatty alcohol of Formula (IV)

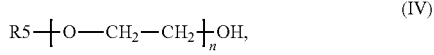

wherein

R5 represents a linear or branched, saturated or unsaturated $C_8$-$C_{24}$ alkyl group, preferably a saturated, linear $C_{16}$ or $C_{18}$ alkyl group and n represents a whole number from about 50 to about 150, preferably a whole number from about 80 to about 120, furthermore preferably the number 100, wherein the at least one fatty alcohol of Formula (IV) is contained preferably in a total amount of from about 0.03-about 0.3% by weight, especially of from about 0.08 to about 0.25% by weight and particularly of from about 0.1-about 0.2% by weight, at least one polyol, selected from $C_2$-$C_9$ alkanols with 2-6 hydroxyl groups and polyethylene glycols with 3-20 ethylene oxide units as well as mixtures hereof, preferably in a total amount of from about 1-about 10% by weight, especially of from about 2-about 8% by weight and particularly of from about 3-about 6% by weight and at least one oil, preferably in a total amount of from about 0.1-about 5% by weight, particularly of from about 0.2-about 3% by weight and more particularly of from about 0.5-about 2.5% by weight, wherein all quantitative data is related to the weight of the oxidizing composition; and the composition (A) is present in the form of a soap-based gel and from about 25-about 85% by weight of water, ammonia, from about 5-about 20% by weight and preferably from about 8-about 16% by weight of a salt of a $C_{12}$-$C_{22}$ fatty acid, preferably a salt of oleic acid, from about 2-about 20% and preferably from about 3-about 16% by weight of at least one polyethylene glycol ether of a linear, saturated or unsaturated $C_{10}$-$C_{18}$ alkanols with 1-5 ethylene oxide units in the molecule, from about 0-about 1% by weight of at least one oil, preferably at least one organic solvent, selected from a monohydric to a tetrahydric $C_2$-$C_6$ alcohols, a total amount of from about 0.1-about 35% by weight being particularly preferred optionally from about 0.1-about 3% by weight of an anionic surfactant selected from alkyl sulfates, alkyl ether sulfates and ether carboxylic acids with 10 to 20 carbon atoms in the alkyl group and up to 16 glycol ether groups in the molecule, and optionally at least one oxidizing dye precursor are contained and has a pH ranging from about 8 to about 11.5, measured at 20° C., wherein all quantitative data is related to the weight of composition (A);

wherein the compositions (A) and (B) are present in a ratio by weight (A)/(B) ranging from about 0.33-about 3, preferably from about 0.5-about 2 and particularly 1:1.

The composition (A) corresponds to the above-described alkalizing preparation.

Composition (A) contains ammonia and optionally at least one further alkalizing agent, which is selected from the group comprising alkanolamines, basic amino acids, as well as inorganic alkalizing agents such as alkaline (earth) alkali metal hydroxides, alkaline (earth) methyl meta-silicates, alkaline (earth) metal phosphates and (alkaline (earth) metal hydrogen phosphates Sodium hydroxide, potassium hydroxide, sodium silicate and sodium metasilicates are suitable inorganic alkalizing agents. Organic alkalizing agents which can be used as contemplated herein, preferably are selected from monoethanolamine, 2-amino-2-methylpropanol and triethanolamine. The basic amino acids, which can be used as alkalizing agents as contemplated herein, preferably are selected from the group comprising arginine, lysine, ornithine and histidine, arginine being particularly preferred. Usually, ammonia ($NH_3$) is used in the form of an aqueous solution. Aqueous ammonia solutions frequently contain ammonia ($NH_3$) in concentrations of from about 10 to about 32% by weight. The use of an aqueous ammonia solution, which contains 25% by weight of ammonia ($NH_3$) is preferred here. Preferably, the total amount of alkalizing agent is selected so that the mixture of the ready-to-use dyeing composition has an alkaline pH, preferably a pH of from about 8 to about 11.5, particularly of from about 8.5 to about 11 and especially a pH of from about 9.0 to about 10.5. Preferably, ammonia and optionally monoethanolamine are contained in the composition (A) used as contemplated herein in amounts of from about 0.01-about 10% by weight, particularly of from about 0.1 to about 7.5% by weight, especially of from about 0.2 to about 5.5% by weight and more especially from about 0.4 to about 4.5% by weight, based in each case on the weight of the composition (A), so that the pH of the composition (A) ranges from about 8 to about 11.5, measured at 20° C.

As optional components, the alkalizing composition (A), which is used as contemplated herein, contains at least one oxidizing dye precursor, which preferably is selected from one or more developer components and optionally one or more coupling components.

Preferably, at least one oxidizing dye precursor is contained in a total amount of from about 0.0001 to about 10.0% by weight and particularly of from about 0.01 to about 8% by weight, based in each case on the weight of the total composition (A).

It may be preferred as contemplated herein to select at least one compound from the group comprising p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazole-1-yl)propyl]amine, N,N'-bis-(2-hydroxyethyl)-N,N'-bis-(4-aminophenyl)-1,3-diamino-propan-2-ol, bis-(2-hydroxy-5- aminophenyl)methane, 1,3-bis-(2,5-diaminophenoxy)-propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methyl-phenol, 4-amino-2-aminomethylphenol, 4-amino-2-(1,2-dihydroxyethyl)phenol, 4-amino-2-(diethyl-aminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, as well as their physiologically tolerated salts.

Preferably, at least one oxidizing dye precursor is contained in a total amount of from about 0.0001 to about 10.0% by weight and particularly of from about 0.01 to about 8% by weight, based in each case on the weight of the total composition (A).

Within the context of oxidative dyeing, coupler components alone do not produce significant dyeing and always require the presence of developer components. It is therefore preferred as contemplated herein that, when at least one developer component is used, at least one coupler component is used.

Coupler components, preferred as contemplated herein, are selected from the group comprising 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2-hydroxyethyl)amino-2-methylphenol, 3-(diethylamino) phenol, N-cyclopentyl-3-aminophenol, 1,3-dihydroxy-5-(methylamino)benzene, 3-ethylamino-4-methylphenol, 2,4-dichloro-3-aminophenol, 2-(2,4diaminophenoxy)ethanol, 1,3-bis-(2,4-diaminophenoxy) propane, 1-methoxy-2-amino-4-(2-hydroxyethylamino) benzene, 1,3-bis-(2,4-diaminophenyl) propane, 2,6-bis-(2'-hydroxyethylamino)-1-methylbenzene, 2-({3-[(2-hydroxy-ethyl)amino]-2-methoxy-5-methylphenyl}amino)ethanol, 2-({3-[(2-hydroxyethyl(amino]-2-methoxy-5-methylphenyl}amino) ethanol, 2-({3-[(2-hydroxyethyl)amino]-4,5-dimethylphenyl}amino)ethanol, 2-[3-morpholine-4-ylphenyl)amino]ethanol, 3-amino-4-(2-methoxyethoxy)-5-methylphenylamine, 1-amino-3-bis-(2-hydroxyethyl) aminobenzene, resorcinol, resorcinol monomethyl ether, 2-methylresorcinol, 5-methylresorcinol, 2,5-dimethylresorcinol, 2-chlororesorcinol, 4-chlororesorcinol, pyrogallol, 1,2,4-trihydroxybenzene, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-demethoxypyridine, 2,6-dihydroxy-3,4-dimethylpyridine, 3,4-diaminopyridine, 2-(2-methoxyethyl)amino-3-amino-6-methoxypyridine, 2-(4'-methoxyphenyl) amino-3-aminopyridine, 1-naphthol, 2-methyl-1-naphthol, 2-hydroxymethyl-1-naphthol, 2-hydroxyethyl-1-naphthol, 1,3-dihydroxynaphthalene, 1,5-dihydroxy naphthalene, 1,6-dihydroxynaphthalene, 1,7-dihydroxynaphthalene, 1,8-dihydroxynaphthalene, 2,7-dihydroxynaphthalene, 2,3-dihydroxynaphthalene, 4-hydroxyindole, 6-hydroxyindole, 7-hydroxyindole, 4-hydroxyindoline, 6-hydroxyindoline, 7-hydroxyindoline, 4,6-diaminopyrimidine, 4-amino-2,6-dihydroxy-pyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine or mixtures of these compounds or their physiologically tolerated salts.

Preferably, at least one coupler component is contained in a total amount of from about 0.0001 to about 10.0% by weight and particularly of from about 0.01 to about 8% by weight, based in each case on the weight of the total composition (A).

For this purpose, the developer components and coupler components generally are used in about equimolar amounts. Even if the equimolar use has proven to be appropriate, an excess of individual oxidation dye precursors is not disadvantageous, so that the developer components and keratinic fibers are exemplified in that the aforementioned coupler component as contemplated herein may be contained in a molar ratio of from about 1:0.5 to about 1:3 and especially from about 1:1 to about 1:2.

Preferred kits as contemplated herein for the oxidative color change of keratinic fibers are exemplified in that the aforesaid oxidation composition (B) and the aforementioned alkalizing composition (A) are contained in a ratio A/B by weight of from about 0.33 to about 3, particularly preferably of from about 0.5 to about 2 and extraordinarily preferably in the ratio by weight of 1:1.

Kits for the oxidative color change of keratinic fibers, which are particularly preferred as contemplated herein, are exemplified in that the above-mentioned inventive or preferred as contemplated herein oxidation composition (B) and the above-named alkalizing composition (A) are present in a weight ratio A/B of from about 0.33 to about 3, more preferably from about 0.5 to about 2 and particularly preferably in a weight ratio of 1:1, the kit containing no further components added to the ready-for-use color-changing mixture, while components for pre-treatment or after-treatment of the keratinic fibers, for example conditioners or shampoos, may be contained in the kit.

In a preferred embodiment as contemplated herein, the kit as contemplated herein is exemplified in that the composition (A), in each case based on its weight, contains from about 25-about 85% by weight of water, ammonia, from about 5-about 20% by weight and preferably from about 8-about 16% of at least one salt of a $C_{12}$-$C_{22}$ fatty acid, preferably a salt of oleic acid, optionally from about 0.1-about 3% by weight of an anionic surfactant, selected from alkyl sulfates, alkyl ether sulfates and ether carboxylic acids having 10 to 20 carbon atoms in the alkyl group and up to 16 glycol ether groups in the molecule, from about 2-about 20% by weight and preferably from about 3-about 16% by weight, of at least one polyethylene glycol ether of a linear saturated or unsaturated $C_{10}$-$C_{18}$ alkanol having 1-5 ethylene oxide units in the molecule, from about 0-about 1% by weight of at least one oil, preferably at least one organic solvent selected from mono- to tetrahydric $C_2$-$C_6$ alcohols, more preferably in a total quantity of from about 0.1-about 35% by weight and, if appropriate, at least one oxidation dye precursor and having a pH in the range from about 8 to about 11.5, measured at 20° C.

With regard to further preferred embodiments of the kit as contemplated herein what has been said in regard to the oxidation compositions as contemplated herein as well as to the alkalizing compositions (A), used as contemplated herein, applies mutatis mutandis.

A further subject matter of the present disclosure is a method for oxidatively changing the color of keratinic fibers, which is exemplified by the following process steps:

Providing an oxidizing composition (B) according to any one of claims 1-8, containing the providing of an oxidizing composition (B) according to any one of claims 1-8, containing from about 50-about 96% by weight, preferably from about 70-about 93% by weight particularly from about 80-about 90% by weight of water from about 0.5-about 20% by weight of hydrogen peroxide, at least one linear, saturated 1-alkanol with 12-30 carbon atoms, preferably in a total amount of from about 2-about 8% by weight and particularly of from about 3 to about 6.5% by weight, at least one glyceryl fatty acid ester of the general Formula (1),

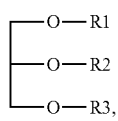
(I)

wherein
R1, R2 and R3 independently of one another represent a hydrogen atom or a group of Formula (II) (II)

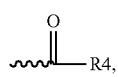
(II)

wherein
R4 represents a linear or branched, saturated or unsaturated $C_{11}$-$C_{27}$ alkyl group with the proviso that at least one and not more than two groups are selected from R1, R2 and R3 for a grouping of Formula (II), the at least one glyceryl fatty acid ester of the general Formula (I) preferably is contained in a total amount of from about 0.01-about 1% by weight particularly of from about 0.1 to about 0.8% by weight, at least one ethoxylated fatty alcohol of Formula (III)

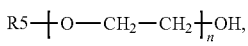
(III)

wherein
R5 represents an or branched, saturated or unsaturated $C_8$-$C_{24}$ alkyl group, preferably a saturated, linear $C_{16}$ or $C_{18}$ alkyl group and n represents a whole number from 10 to 30, preferably a whole number from 12 to 25, furthermore preferably for a whole number of 15 to 20, wherein the at least one ethoxylated fatty alcohol of Formula (III) preferably is contained in a total amount of from about 0.25-about 2% by weight and particularly of from about 0.5 to about 1.5% by weight, at least one ethoxylated fatty alcohol of Formula (IV)

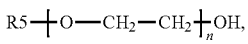
(IV)

wherein
R5 represents a linear or branched, saturated or unsaturated $C_8$-$C_{24}$ alkyl group, preferably a saturated, linear $C_{16}$ or $C_{18}$ alkyl group and n represents a whole number from about 50 to about 150, preferably a whole number from about 80 to about 120, furthermore preferably for the number 100, wherein the at least one ethoxylated fatty alcohol of Formula (IV) is contained preferably in a total amount of from about 0.03-about 0.3% by weight, preferably in amount of from about 0.08 to about 0.25% by weight and particularly in an amount of from about 0.1-about 0.2% by weight, at least one polyol, selected from $C_2$-$C_9$ alkanols with 2-6 hydroxyl groups and polyethylene glycols with 3-20 ethylene oxide units as well as mixtures hereof, preferably in a total amount of from about 1-about 10% by weight, especially of from about 2-about 8% by weight and particularly of from about 3-about 6% by weight and at least one oil, preferably in a total amount of from about 0.1-about 5% by weight, particularly of from about 0.2-about 3% by weight and more particularly of from about 0.5-about 2.5% by weight, wherein all quantitative data is related to the weight of the oxidizing composition, and the composition (A) is provided in the form of a soap-based gel containing from about 25-about 85% by weight of water, ammonia, from about 5-about 20% by weight of water, preferably from about 8 to about 16% by weight of a salt of a $C_{12}$-$C_{22}$ fatty acid, preferably of a salt of oleic acid, from about 2-about 20% and preferably from about 3-about 16% by weight of at least one polyethylene glycol ether of a linear, saturated or unsaturated $C_{10}$-$C_{18}$ alkanols with 1-5 ethylene oxide units in the molecule, a total of from about 0-about 1% by weight of at least one oil, preferably at least one organic solvent, selected from a monohydric to a tetrahydric $C_2$-$C_6$ alcohols, a total amount of from about 0.1-about 35% by weight being particularly preferred optionally from about 0.1-about 3% by weight of an anionic surfactant selected from alkyl sulfates, alkyl ether sulfates and ether carboxylic acids with 10 to 20 carbon atoms in the alkyl group and up to 16 glycol ether groups in the molecule, and optionally at least one oxidizing dye precursor, has a pH ranging from about 8 to about 11.5, measured at 20° C., wherein all quantitative data is related to the weight of composition (A);

preparation of a mixture of the aforementioned oxidizing compositions (B) and of the aforementioned composition (A), preferably in a weight related ratio of mixing (A)/(B) ranging from about 0.33-about 3, especially from about 0.5-about 2 and particularly 1:1, immediately afterwards the ready-to-use composition is distributed on the fibers, the composition remains on the fibers for a period from about 1 to about 60 minutes, after which the remaining composition is immediately rinsed from the fibers and optionally the fibers are dried.

Methods for the oxidative color change of keratinic fibers, preferred as contemplated herein, are exemplified in that the abovementioned oxidation composition (B) and the abovementioned alkalinizing composition (A) are mixed with one another in the weight-based mixing ratio (A)/(B) ranging from about 0.33-about 3, preferably from about 0.5-about 2 and especially from 1:1.

With regard to further preferred embodiments of the method as contemplated herein, what has been said in regard to the oxidation compositions as contemplated herein applies mutatis mutandis to the alkalizing compositions (A) used as contemplated herein.

Wool, fur, feathers and especially human hair are understood to be keratinic or keratin-containing fibers. In principle, the dyeing and brightening methods as contemplated herein can also be used for other natural fibers such as cotton, jute, sisal, linen, silk or modified natural fibers such as the regenerated cellulose, nitro-, alkyl-, or hydroxyalkyl- or acetyl cellulose.

The ready-to-use dyeing agent of the method as contemplated herein preferably is produced by combining the oxidizing compositions as contemplated herein with an alkalizing composition (A), produced, as contemplated herein, in a container, which can be closed off once again, and by subsequently mixing.

In the subsequent step of the method, the ready-to-use dyeing composition is distributed on the keratinic fibers. For the method of changing the color of human hair, the ready-to-use composition is distributed directly on the hair of the user. Preferably, the distribution is manual. For this purpose, the user takes the ready-to-use composition from the mixing container, preferably from the re-closable container, by scooping or pouring the composition into the hand and subsequently distributing and preferably incorporating the composition into the hair of the head. Preferably, direct contact between the ready-to-use color changing composition and the hands is avoided by using suitable gloves, such as disposable latex gloves.

Subsequently, the ready-to-use dyeing composition is left on the fibers to be treated for a period of from about 1 to about 60 minutes. Preferably, the time period ranges from about 10 to about 45 minutes and especially from about 20 to about 30 minutes.

The application temperatures can range from about 15° to about 40° C. Optionally, while the composition remains on the fibers, the temperature can be increased or adjusted to a precisely defined value by external heat sources. It is particularly preferred if the color change is supported by physical measures. Methods as contemplated herein, in which the application is supported by the action of heat, IR radiation and/or UV radiation during the exposure time, may be preferred.

At the end of the exposure time, the ready-to-use or remaining dye is removed from the fibers to be treated by rinsing it out in the last step of the process. For this purpose, the fibers are then rinsed with water and/or an aqueous surfactant preparation. Usually, from about 20° C. to about 40° C. warm water or a correspondingly temperature-controlled aqueous surfactant preparation is used for this purpose. Optionally, further treatment steps may follow, such as the application of a leave-on or rinse-off conditioner, a further dyeing step, such as the coloring or lightening of strands, a hair shaping and/or drying of the hair.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An oxidizing composition for the oxidative treatment of hair, comprising
from about 50-about 96% by weight of water,
from about 0.5-about 20% by weight of hydrogen peroxide,
at least one linear, saturated 1-alkanol with 12-30 carbon atoms,
at least one glyceryl fatty ester of the general Formula (I),

wherein
R1, R2 and R3, independently of one another represent a hydrogen atom or a group of Formula (II),

wherein
R4 represents a linear or branched, saturated or unsaturated $C_{11}$-$C_{27}$ alkyl group,
with the proviso that at least one and not more than two groups are selected from R1, R2 and R3 of a grouping of Formula (II),
at least one ethoxylated fatty alcohol of Formula (III)

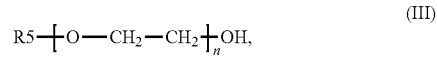

wherein
R5 represents a linear or branched, saturated or unsaturated $C_8$-$C_{24}$ alkyl group, and
n represents a whole number from 15 to 20,
at least one ethoxylated fatty alcohol of Formula (IV)

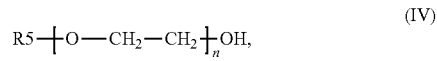

wherein
R5 represents a linear or branched, saturated or unsaturated $C_8$-$C_{24}$ alkyl group, and
n represents a whole number 50 to 150,
at least one polyol, selected from $C_2$-$C_9$ alkanols with 2-6 hydroxyl groups, polyethylene glycols with 3-20 ethylene oxide units, or mixtures thereof, and
at least one oil,
wherein all quantitative data is related to the weight of the oxidizing composition.

2. A kit for oxidatively changing the color of keratinic fibers, comprising two compositions (A) and (B) contained separately from one another, wherein
the composition (B) is an oxidizing composition comprising:
from about 50-about 96% by weight of water,
from about 0.5-about 20% by weight of hydrogen peroxide,
at least one linear, saturated 1-alkanol with 12-30 carbon atoms,
at least one glyceryl fatty ester of the general Formula (I),

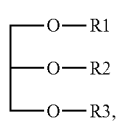

(I)

wherein
R1, R2 and R3, independently of one another represent a hydrogen atom or a group of Formula (II),

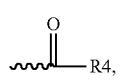

(II)

wherein
R4 represents a linear or branched, saturated or unsaturated $C_{11}$-$C_{27}$ alkyl group,
with the proviso that at least one and not more than two groups are selected from R1, R2 and R3 of a grouping of Formula (II),
at least one ethoxylated fatty alcohol of Formula (III)

(III)

wherein
R5 represents a linear or branched, saturated or unsaturated $C_8$-$C_{24}$ alkyl group, and
n represents a whole number from 10 to 30,
at least one ethoxylated fatty alcohol of Formula (IV)

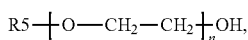

(IV)

wherein
R5 represents a linear or branched, saturated or unsaturated $C_8$-$C_{24}$ alkyl group, and
n represents a whole number from 50 to 150,
at least one polyol, selected from $C_2$-$C_9$ alkanols with 2-6 hydroxyl groups, polyethylene glycols with 3-20 ethylene oxide units, or mixtures thereof, and
at least one oil,
wherein all quantitative data of the composition (B) is related to the weight of the oxidizing composition, and
the composition (A) is present in the form of a soap-based gel present and
from about 25-about 85% by weight of water ammonia,
from about 5-about 20% by weight of a salt of a $C_{12}$-$C_{22}$ fatty acid,
from about 2-about 20% by weight of at least one polyethylene glycol ether of a linear, saturated or unsaturated $C_{10-18}$ alkanols with 1-5 ethylene oxide units in the molecule,
a total of from about 0-about 1% by weight of at least one oil,
optionally at least one organic solvent, selected from a monohydric to tetrahydric $C_2$-$C_6$ alcohols,
optionally from about 0.1-about 3% by weight of an anionic surfactant selected from alkyl sulfates, alkyl ether sulfates and ether carboxylic acids with 10 to 20 carbon atoms in the alkyl group and up to 16 glycol ether groups in the molecule,
optionally at least one oxidizing dye precursor,
wherein composition (A) has a pH ranging of from about 8 to about 11.5, measured at 20° C.,
wherein all quantitative data of the composition (A) is based on the weight of the composition (A).

3. The kit according to claim 2, wherein the at least one linear saturated 1-alkanol having from about 12-about 30 carbon atoms of the composition (B), is selected from lauryl alcohol, myristyl alcohol, cetyl alcohol, stearyl alcohol, arachidyl alcohol, behenyl alcohol, or mixtures of these alkanols.

4. The kit according to claim 2, wherein at least one compound, selected from glyceryl monostearate, glyceryl distearate, glyceryl monopalmitate and glyceryl dipalmitate is used as the glyceryl fatty acid ester of Formula (I) in a total amount of from about 0.01 to about 1% by weight, based on the weight of the oxidizing composition.

5. The kit according to claim 2, wherein the ethoxylated fatty alcohol of Formula (III) is selected from at least one compound of the following:
1-decanol (decyl alcohol), ethoxylated with 10 EO,
1-decanol (decyl alcohol), ethoxylated with 20 EO,
1-decanol (decyl alcohol), ethoxylated with 30 EO,
1-dodecanol (dodecyl alcohol, lauryl alcohol), ethoxylated with 10 EO,
1-dodecanol (dodecyl alcohol), lauryl alcohol), ethoxylated with 20 EO,
1-dodecanol (dodecyl alcohol), lauryl alcohol), ethoxylated with 30 EO,
1-hexadecanol (hexadecyl alcohol, cetyl alcohol, palmityl alcohol), ethoxylated with 10 EO,
1-hexadecanol (hexadecyl alcohol, cetyl alcohol, palmityl alcohol), ethoxylated with 12 EO,
1-hexadecanol (hexadecyl alcohol, cetyl alcohol, palmityl alcohol), ethoxylated with 15 EO,
1-hexadecanol (hexadecyl alcohol, cetyl alcohol, palmityl alcohol), ethoxylated with 20 EO,
1-hexadecanol (hexadecyl alcohol, cetyl alcohol, palmityl alcohol), ethoxylated with 25 EO,
1-hexadecanol (hexadecyl alcohol, cetyl alcohol, palmityl alcohol), ethoxylated with 30 EO,
1-octadecanol (octadecyl alcohol, stearyl alcohol), ethoxylated with 10 EO,
1-octadecanol (octadecyl alcohol, stearyl alcohol), ethoxylated with 12 EO,
1-octadecanol (octadecyl alcohol, stearyl alcohol), ethoxylated with 15 EO,
1-octadecanol (octadecyl alcohol, stearyl alcohol), ethoxylated with 20 EO,
1-octadecanol (octadecyl alcohol, stearyl alcohol), ethoxylated with 25 EO,
1-octadecanol (octadecyl alcohol, stearyl alcohol), ethoxylated with 30 EO,
1-eicosanol (eicosyl alcohol, arachyl alcohol), ethoxylated with 10 EO,
1-eicosanol (eicosyl alcohol, arachyl alcohol), ethoxylated with 12 EO, 1-eicosanol (eicosyl alcohol, arachyl alcohol), ethoxylated with 15 EO,
1-eicosanol (eicosyl alcohol, arachyl alcohol), ethoxylated with 20 EO,
1-eicosanol (eicosyl alcohol, arachyl alcohol), ethoxylated with 25 EO,
1-eicosanol (eicosyl alcohol, arachyl alcohol), ethoxylated with 30 EO,
1-docosanol (docosyl alcohol, behenyl alcohol), ethoxylated with 10 EO,
1-docosanol (docosyl alcohol, behenyl alcohol), ethoxylated with 12 EO,
1-docosanol (docosyl alcohol, behenyl alcohol), ethoxylated with 15 EO,
1-docosanol (docosyl alcohol, behenyl alcohol), ethoxylated with 20 EO,
1-docosanol (docosyl alcohol, behenyl alcohol), ethoxylated with 25 EO,
1-docosanol (docosyl alcohol, behenyl alcohol), ethoxylated with 30 EO, as well as mixtures thereof.

6. The kit according to claim 2, wherein the ethoxylated fatty alcohol of Formula (IV) is selected from at least one compound of the following:
1-hexadecanol (hexadecyl alcohol, cetyl alcohol, palmityl alcohol), ethoxylated with 50 EO,
1-hexadecanol (hexadecyl alcohol, cetyl alcohol, palmityl alcohol), ethoxylated with 51 EO,
1-hexadecanol (hexadecyl alcohol, cetyl alcohol, palmityl alcohol), ethoxylated with 52 EO,
1-hexadecanol (hexadecyl alcohol, cetyl alcohol, palmityl alcohol), ethoxylated with 53 EO,
1-hexadecanol (hexadecyl alcohol, cetyl alcohol, palmityl alcohol), ethoxylated with 54 EO,
1-hexadecanol (hexadecyl alcohol, cetyl alcohol, palmityl alcohol), ethoxylated with 55 EO,
1-hexadecanol (hexadecyl alcohol, cetyl alcohol, palmityl alcohol), ethoxylated with 56 EO,
1-hexadecanol (hexadecyl alcohol, cetyl alcohol, palmityl alcohol), ethoxylated with 57 EO,
1-hexadecanol (hexadecyl alcohol, cetyl alcohol, palmityl alcohol), ethoxylated with 58 EO,
1-hexadecanol (hexadecyl alcohol, cetyl alcohol, palmityl alcohol), ethoxylated with 59 EO,
1-hexadecanol (hexadecyl alcohol, cetyl alcohol, palmityl alcohol), ethoxylated with 60 EO,
1-hexadecanol (hexadecyl alcohol, cetyl alcohol, palmityl alcohol), ethoxylated with 90 EO,
1-hexadecanol (hexadecyl alcohol, cetyl alcohol, palmityl alcohol), ethoxylated with 91 EO,
1-hexadecanol (hexadecyl alcohol, cetyl alcohol, palmityl alcohol), ethoxylated with 92 EO,
1-hexadecanol (hexadecyl alcohol, cetyl alcohol, palmityl alcohol), ethoxylated with 93 EO,
1-hexadecanol (hexadecyl alcohol, cetyl alcohol, palmityl alcohol), ethoxylated with 94 EO,
1-hexadecanol (hexadecyl alcohol, cetyl alcohol, palmityl alcohol), ethoxylated with 95 EO,
1-hexadecanol (hexadecyl alcohol, cetyl alcohol, palmityl alcohol), ethoxylated with 96 EO,
1-hexadecanol (hexadecyl alcohol, cetyl alcohol, palmityl alcohol), ethoxylated with 97 EO,
1-hexadecanol (hexadecyl alcohol, cetyl alcohol, palmityl alcohol), ethoxylated with 98 EO,
1-hexadecanol (hexadecyl alcohol, cetyl alcohol, palmityl alcohol), ethoxylated with 99 EO,
1-hexadecanol (hexadecyl alcohol, cetyl alcohol, palmityl alcohol), ethoxylated with 100 EO,
1-hexadecanol (hexadecyl alcohol, cetyl alcohol, palmityl alcohol), ethoxylated with 101 EO,
1-hexadecanol (hexadecyl alcohol, cetyl alcohol, palmityl alcohol), ethoxylated with 102 EO,
1-hexadecanol (hexadecyl alcohol, cetyl alcohol, palmityl alcohol), ethoxylated with 103 EO,
1-hexadecanol (hexadecyl alcohol, cetyl alcohol, palmityl alcohol), ethoxylated with 104 EO,
1-hexadecanol (hexadecyl alcohol, cetyl alcohol, palmityl alcohol), ethoxylated with 105 EO,
1-hexadecanol (hexadecyl alcohol, cetyl alcohol, palmityl alcohol), ethoxylated with 106 EO,
1-hexadecanol (hexadecyl alcohol, cetyl alcohol, palmityl alcohol), ethoxylated with 107 EO,
1-hexadecanol (hexadecyl alcohol, cetyl alcohol, palmityl alcohol), ethoxylated with 108 EO,
1-hexadecanol (hexadecyl alcohol, cetyl alcohol, palmityl alcohol), ethoxylated with 109 EO,
1-hexadecanol (hexadecyl alcohol, cetyl alcohol, palmityl alcohol), ethoxylated with 110 EO,
1-octadecanol (octadecyl alcohol, stearyl alcohol), ethoxylated with 50 EO,
1-octadecanol (octadecyl alcohol, stearyl alcohol), ethoxylated with 51 EO,
1-octadecanol (octadecyl alcohol, stearyl alcohol), ethoxylated with 52 EO,
1-octadecanol (octadecyl alcohol, stearyl alcohol), ethoxylated with 53 EO,
1-octadecanol (octadecyl alcohol, stearyl alcohol), ethoxylated with 54 EO,
1-octadecanol (octadecyl alcohol, stearyl alcohol), ethoxylated with 55 EO,
1-octadecanol (octadecyl alcohol, stearyl alcohol), ethoxylated with 56 EO,
1-octadecanol (octadecyl alcohol, stearyl alcohol), ethoxylated with 57 EO,
1-octadecanol (octadecyl alcohol, stearyl alcohol), ethoxylated with 58 EO,
1-octadecanol (octadecyl alcohol, stearyl alcohol), ethoxylated with 59 EO,
1-octadecanol (octadecyl alcohol, stearyl alcohol), ethoxylated with 60 EO,
1-octadecanol (octadecyl alcohol, stearyl alcohol), ethoxylated with 90 EO,
1-octadecanol (octadecyl alcohol, stearyl alcohol), ethoxylated with 91 EO,
1-octadecanol (octadecyl alcohol, stearyl alcohol), ethoxylated with 92 EO,
1-octadecanol (octadecyl alcohol, stearyl alcohol), ethoxylated with 93 EO,
1-octadecanol (octadecyl alcohol, stearyl alcohol), ethoxylated with 94 EO,
1-octadecanol (octadecyl alcohol, stearyl alcohol), ethoxylated with 95 EO,
1-octadecanol (octadecyl alcohol, stearyl alcohol), ethoxylated with 96 EO,
1-octadecanol (octadecyl alcohol, stearyl alcohol), ethoxylated with 97 EO,
1-octadecanol (octadecyl alcohol, stearyl alcohol), ethoxylated with 98 EO,
1-octadecanol (octadecyl alcohol, stearyl alcohol), ethoxylated with 99 EO,
1-octadecanol (octadecyl alcohol, stearyl alcohol), ethoxylated with 100 EO,
1-octadecanol (octadecyl alcohol, stearyl alcohol), ethoxylated with 101 EO, 1-octadecanol (octadecyl alcohol, stearyl alcohol), ethoxylated with 102 EO,
1-octadecanol (octadecyl alcohol, stearyl alcohol), ethoxylated with 103 EO,
1-octadecanol (octadecyl alcohol, stearyl alcohol), ethoxylated with 104 EO,
1-octadecanol (octadecyl alcohol, stearyl alcohol), ethoxylated with 105 EO,
1-octadecanol (octadecyl alcohol, stearyl alcohol), ethoxylated with 106 EO,
1-octadecanol (octadecyl alcohol, stearyl alcohol), ethoxylated with 107 EO,
1-octadecanol (octadecyl alcohol, stearyl alcohol), ethoxylated with 108 EO,
1-octadecanol (octadecyl alcohol, stearyl alcohol), ethoxylated with 109 EO,
1-octadecanol (octadecyl alcohol, stearyl alcohol), ethoxylated with 110 EO, or mixtures thereof.

7. The kit according to claim 2, wherein the at least one polyol is selected from 1,2-propylene glycol, glycerol, butylene glycols, pentylene glycols, hexanediols, hexanetriols, 1,2-octanediol, 1,8-octanediol, dipropylene glycol, tripropylene glycol, diglycerol, triglycerol, erythritol, sorbitol, PEG-3, PEG-6, PEG-7, PEG-8, or mixtures of the above-mentioned substances.

8. The kit according to claim 2, wherein the at least one oil of composition (B) is selected from natural hydrocarbons; synthetic hydrocarbons; the benzoate esters of linear or branched $C_{8-22}$ alkanols; fatty alcohols with 6-30 carbon atoms, which are unsaturated or branched and saturated or branched and unsaturated; triglycerides of linear or branched, saturated or unsaturated, optionally hydroxylated $C_{8-30}$ fatty acids; the dicarboxylate esters of linear or branched $C_2$-$C_{10}$ alkanols; the esters of linear or branched, saturated or unsaturated fatty alcohols with 2-30 carbon atoms with linear or branched, saturated or unsaturated fatty acids with 2-30 carbon atoms, which may be hydroxylated; the addition products of 1 to 5 propylene oxide units and monohydric or multi-hydric $C_{8-22}$ alkanols; the addition products of at least 6 ethylene oxide units and/or propylene oxide units and monohydric or multihydric $C_{3-22}$ alkanols; the $C_8$-$C_{22}$ fatty alcohol esters of monohydric or multi-hydric $C_2$-$C_7$ hydroxycarboxylic acids; the symmetrical, asymmetrical or cyclic esters of carbonic acid with $C_{3-22}$ alkanols, $C_{3-22}$ alkane diols or $C_{3-22}$ alkane triols; the esters of dimers of unsaturated $C_{12}$-$C_{22}$ fatty acids (dimer fatty acids) with monohydric linear branched or cyclic $C_2$-$C_{18}$ alkanols or with polyhydric linear or branched $C_2$-$C_6$ alkanols; silicone oils; or mixtures of the aforementioned substances.

9. The kit according to claim 2, comprising at least one lamellar phase.

10. A method of oxidatively changing the color of keratinic fibers, comprising the following steps:
providing an oxidizing composition (B), comprising:
from about 50-about 96% by weight of water
from about 0.5-about 20% by weight of hydrogen peroxide,
at least one linear, saturated 1-alkanol with 12-30 carbon atoms,
at least one glyceryl fatty acid ester of the general Formula (I),

wherein
R1, R2 and R3 independently of one another represent a hydrogen atom or a group of Formula (II)

wherein
R4 represents a linear or branched, saturated or unsaturated $C_{11}$-$C_{27}$ alkyl group,
with the proviso that at least one and not more than two groups are selected from R1, R2 and R3 of a grouping of Formula (II),
at least one ethoxylated fatty alcohol of Formula (III)

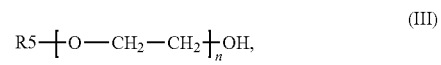

wherein
R5 represents a linear or branched, saturated or unsaturated $C_8$-$C_{24}$ alkyl group, and
n represents a whole number from 10 to 30,
at least one ethoxylated fatty alcohol of Formula (IV)

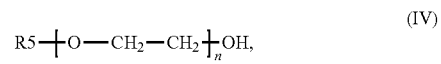

wherein
R5 represents a linear or branched, saturated or unsaturated $C_8$-$C_{24}$ alkyl group, and
n represents a whole number from about 50 to about 150,
at least one polyol selected from C2-C9 alkanols with 2-6 hydroxyl groups, polyethylene glycols with 3-20 ethylene oxide units, or mixtures thereof, and
at least one oil,
wherein all quantitative data of the oxidizing composition (B) is related to the weight of the oxidizing composition and
providing a composition (A), which is present in the form of a soap-based gel and comprises
from about 25-about 85% by weight of water,
ammonia,
from about 5-about 20% by weight of at least one salt of a $C_{12}$-$C_{22}$ fatty acid,
from about 2-about 20% of at least one polyethylene glycol ether of a linear, saturated or unsaturated $C_{10}$-$C_{18}$ alkanols with 1-5 ethylene oxide units in the molecule,
a total of from about 0-about 1% by weight of at least one oil,
optionally at least one organic solvent, selected from monohydric to tetrahydric $C_2$-$C_6$ alcohols, optionally from about 0.1-about 3% by weight of an anionic surfactant selected from alkyl sulfates, alkyl ether sulfates and ether carboxylic acids with 10 to 20 carbon atoms in the alkyl group and up to 16 glycol ether groups in the molecule, and optionally at least one oxidizing dye precursor, wherein composition (A) has a pH ranging from about 8 to about 11.5, measured at 20° C., wherein all quantitative data of composition (A) is related to the weight of the composition (A);

preparing a mixture of the aforementioned oxidizing composition (B) and of the aforementioned composition (A);

immediately thereafter distributing the ready-to-use composition on the fibers;

leaving the composition on the fibers for a period of from about 1 to about 60 minutes, after which the remaining composition is immediately rinsed from the fibers and optionally drying the fibers.

11. The kit of claim 2, wherein composition (B) comprises from about 80-about 90% by weight of water.

12. The kit of claim 2, wherein the at least one linear saturated 1-alkanol with 12-30 carbon atoms is present in a total amount of from about 2-8% by weight, based on the weight of the oxidative composition.

13. The kit of claim 2, wherein the at least one glyceryl fatty acid ester of the general Formula (I) is present in a total amount of from about 0.01-about 1% by weight, based on the weight of the oxidative composition.

14. The kit of claim 2, wherein in the at least one ethoxylated fatty alcohol of the formula (III) R5 stands for a saturated unbranched $C_{16}$ or $C_{18}$ alkyl group and n stands for an integer from 15 to 20.

15. The kit of claim 2, wherein the at least one ethoxylated fatty alcohol of formula (III) is present in a total amount of from about 0.25-2% by weight, based on the weight of the oxidative composition.

16. The kit of claim 2, wherein in the at least one ethoxylated fatty alcohol of formula (IV) R5 stands for a saturated linear $C_{16}$ or $C_{18}$ alkyl group and n stands for a whole number from about 80 to about 120.

17. The kit of claim 2, wherein the at least one ethoxylated fatty alcohol of formula (IV) is present in a total amount of from about 0.03-0.3% by weight, based on the weight of the oxidative composition.

18. The kit of claim 2, wherein the at least one polyol selected from $C_2$-$C_9$ alkanols with 2-6 hydroxyl groups, polyethylene glycols with 3-20 ethylene oxide units, or mixtures thereof is present in a total amount of from about 1-10% by weight, based on the weight of the oxidative composition.

19. The kit of claim 2, wherein the at least one oil of the oxidative composition (B) is present in a total amount of from about 0.1-5% by weight, based on the weight of the oxidative composition.

20. The kit of claim 2, wherein the composition (B) comprises:

from about 80-90% by weight water, and wherein;

the at least one linear saturated 1-alkanol with 12-30 carbon atoms present in an amount of from about 3 to 6.5% by weight, the at least one mono- or diester of ethylene glycol with palmitic acid and/or stearic acid as well as mixtures thereof present in an amount of from about 0.1 to 0.8% by weight, the at least one ethoxylated fatty alcohol of the formula (III) where R5 stands for a saturated unbranched $C_{16}$ or $C_{18}$ alkyl group and n stands for an integer from 15 to 20, wherein the at least one ethoxylated fatty alcohol of formula (III) is present in a total amount of from about 0.5 to 1.5% by weight, the at least one ethoxylated fatty alcohol of formula (IV) where R5 stands for a saturated unbranched $C_{16}$ or $C_{18}$ alkyl group and n stands for an integer from 80 to about 120, wherein the at least one ethoxylated fatty alcohol of formula (IV) is present in a total amount of from about 0.1-0.2% by weight, the at least one polyol is present in an amount of from about 3-6% by weight, and the at least one oil is present in an amount of from about 0.5-2.5% by weight, wherein all the quantitative amounts are based on the weight of the oxidative composition.

* * * * *